(12) United States Patent
Burns et al.

(10) Patent No.: US 8,551,047 B2
(45) Date of Patent: Oct. 8, 2013

(54) FLUID DELIVERY DEVICES, SYSTEMS AND METHODS

(75) Inventors: John Burns, Austin, TX (US); William Atkinson, Fallbrook, CA (US); Raymond Clark, Valley Center, CA (US); Darrin Schmuckle, San Marcos, CA (US); Chris Donnelly, Austin, TX (US); Kate Ferguson, Austin, TX (US); Brandon Turner, Austin, TX (US); Dan Benzon, Austin, TX (US); Nikhil Dixit, Houston, TX (US); Catherine Patton, Austin, TX (US)

(73) Assignee: Patton Medical Devices, LP, Austin, TX (US)

( * ) Notice: Subject to any disclaimer, the term of this patent is extended or adjusted under 35 U.S.C. 154(b) by 1123 days.

(21) Appl. No.: 11/466,349

(22) Filed: Aug. 22, 2006

(65) Prior Publication Data
US 2008/0021375 A1    Jan. 24, 2008

Related U.S. Application Data

(60) Provisional application No. 60/710,315, filed on Aug. 22, 2005.

(51) Int. Cl.
*A61M 5/178* (2006.01)
*A61M 37/00* (2006.01)

(52) U.S. Cl.
USPC ............................. 604/167.02; 604/288.02

(58) Field of Classification Search
USPC ............... 604/167.02, 180, 288.01–288.04
See application file for complete search history.

(56) References Cited

U.S. PATENT DOCUMENTS

| | | | |
|---|---|---|---|
| 3,547,119 A | 12/1970 | Hall et al. | 128/214.4 |
| 3,620,209 A | 11/1971 | Kravitz | 601/79 |
| 4,311,137 A | 1/1982 | Gerard | 128/214.4 |
| 4,315,513 A | 2/1982 | Nawash et al. | 128/348 |
| 4,525,164 A | 6/1985 | Loeb et al. | 604/131 |
| 4,531,937 A | 7/1985 | Yates | 604/53 |
| 4,568,335 A | 2/1986 | Updike et al. | 604/211 |
| 4,578,063 A | 3/1986 | Inman et al. | 604/175 |
| 4,675,006 A | 6/1987 | Hrushesky | 604/180 |
| 4,755,173 A | 7/1988 | Konopka et al. | 604/167 |
| 4,772,261 A | 9/1988 | Von Hoff et al. | 604/51 |
| 4,817,631 A | 4/1989 | Schnepp-Pesch et al. | 128/753 |
| 4,874,377 A | 10/1989 | Newgard et al. | 604/167 |

(Continued)

FOREIGN PATENT DOCUMENTS

| | | |
|---|---|---|
| DE | 19912459 A1 | 9/2000 |
| DE | 19912459 C2 | 2/2001 |

(Continued)

OTHER PUBLICATIONS

Altman et al., "The Revised CONSORT Statement for Reporting Randomized Trials: Explanation and Elaboration," *Annals Internal Medicine*, 134:663-694, 2001.

(Continued)

*Primary Examiner* — Kevin C Sirmons
*Assistant Examiner* — Andrew Gilbert
(74) *Attorney, Agent, or Firm* — Fulbright & Jaworski LLP

(57) ABSTRACT

Fluid delivery devices, systems and methods. Some of the fluid delivery devices include a body, a cannula and a septum, and are suited for enabling the delivery of fluid to a user.

6 Claims, 29 Drawing Sheets

(56) References Cited

U.S. PATENT DOCUMENTS

| | | | |
|---|---|---|---|
| 4,966,588 A | 10/1990 | Rayman et al. | 604/165.02 |
| 5,080,654 A | 1/1992 | Picha et al. | 604/167 |
| 5,092,849 A | 3/1992 | Sampson | 604/175 |
| 5,108,377 A | 4/1992 | Cone et al. | 604/175 |
| 5,122,114 A | 6/1992 | Miller et al. | 604/49 |
| 5,176,653 A | 1/1993 | Metals | 604/167.02 |
| 5,176,662 A | 1/1993 | Bartholomew et al. | 604/513 |
| 5,257,980 A | 11/1993 | Van Antwerp et al. | 604/506 |
| 5,306,243 A | 4/1994 | Bonaldo | 604/86 |
| 5,332,398 A | 7/1994 | Miller et al. | 604/175 |
| 5,342,316 A | 8/1994 | Wallace | 604/167 |
| 5,370,625 A | 12/1994 | Shichman | 604/174 |
| 5,409,466 A | 4/1995 | Watson et al. | 604/198 |
| 5,522,803 A | 6/1996 | Teissen-Simony | 604/177 |
| 5,545,143 A | 8/1996 | Fischell | 604/180 |
| 5,545,152 A | 8/1996 | Funderburk et al. | 604/283 |
| 5,569,206 A | 10/1996 | Gorman et al. | 604/167.01 |
| 5,584,813 A | 12/1996 | Livingston et al. | 604/177 |
| 5,607,407 A | 3/1997 | Tolkoff et al. | 604/282 |
| 5,618,295 A | 4/1997 | Min | 606/171 |
| 5,647,851 A | 7/1997 | Pokras | 604/131 |
| 5,718,682 A | 2/1998 | Tucker | 604/93 |
| 5,727,770 A | 3/1998 | Dennis | 251/149.1 |
| 5,749,861 A | 5/1998 | Guala et al. | 604/249 |
| 5,797,879 A | 8/1998 | DeCampli | 604/93.01 |
| 5,839,895 A | 11/1998 | Fishburne, Jr. | 433/118 |
| 5,848,989 A | 12/1998 | Villani | 604/288.02 |
| 5,851,197 A | 12/1998 | Marano et al. | 604/135 |
| 5,871,500 A | 2/1999 | Jepson et al. | 604/533 |
| 5,873,844 A | 2/1999 | Campero et al. | 601/2 |
| 5,925,017 A | 7/1999 | Kriesel et al. | 604/132 |
| 5,951,521 A | 9/1999 | Mastrototaro et al. | 604/174 |
| 5,954,684 A | 9/1999 | Flower et al. | 604/20 |
| 5,954,687 A | 9/1999 | Baudino | 604/48 |
| 5,968,011 A | 10/1999 | Larsen et al. | 604/288.02 |
| 5,980,506 A | 11/1999 | Mathiasen | 604/535 |
| 5,989,224 A | 11/1999 | Exline et al. | 604/167.02 |
| 6,017,328 A | 1/2000 | Fischell et al. | 604/180 |
| 6,056,718 A | 5/2000 | Funderburk et al. | 604/93.01 |
| 6,068,613 A | 5/2000 | Kriesel et al. | 604/132 |
| 6,074,371 A | 6/2000 | Fischell | 604/207 |
| 6,086,575 A | 7/2000 | Mejslov | 604/533 |
| 6,093,172 A | 7/2000 | Funderburk et al. | 604/135 |
| 6,110,154 A | 8/2000 | Shimomura et al. | 604/256 |
| 6,123,690 A | 9/2000 | Mejslov | 604/283 |
| 6,176,235 B1 | 1/2001 | Benarrouch et al. | 128/200.24 |
| 6,231,531 B1 | 5/2001 | Lum et al. | 601/46 |
| 6,254,586 B1 | 7/2001 | Mann et al. | 604/506 |
| 6,293,925 B1 | 9/2001 | Safabash et al. | 604/136 |
| 6,302,866 B1 | 10/2001 | Marggi | 604/174 |
| 6,344,033 B1 | 2/2002 | Jepson et al. | 604/256 |
| 6,355,021 B1 | 3/2002 | Nielsen et al. | 604/263 |
| 6,387,098 B1 | 5/2002 | Cole et al. | 606/62 |
| 6,413,244 B1 | 7/2002 | Bestetti et al. | 604/256 |
| 6,461,329 B1 | 10/2002 | Van Antwerp et al. | 604/111 |
| 6,488,663 B1 | 12/2002 | Steg | 604/164.08 |
| 6,520,938 B1 * | 2/2003 | Funderburk et al. | 604/164.08 |
| 6,572,586 B1 * | 6/2003 | Wojcik | 604/165.01 |
| 6,579,267 B2 | 6/2003 | Lynch et al. | 604/174 |
| 6,585,695 B1 | 7/2003 | Adair et al. | 604/183 |
| 6,602,229 B2 | 8/2003 | Coss | 604/187 |
| 6,629,949 B1 | 10/2003 | Douglas | 604/46 |
| 6,641,566 B2 | 11/2003 | Douglas et al. | 604/218 |
| 6,659,982 B2 | 12/2003 | Douglas et al. | 604/173 |
| 6,673,440 B2 | 1/2004 | Douglas et al. | 428/336 |
| 6,685,674 B2 * | 2/2004 | Douglas et al. | 604/167.05 |
| 6,699,218 B2 | 3/2004 | Flaherty et al. | 604/131 |
| 6,702,761 B1 | 3/2004 | Damadian et al. | 600/576 |
| 6,736,797 B1 | 5/2004 | Larsen et al. | 604/167.05 |
| 6,749,587 B2 | 6/2004 | Flaherty | 604/151 |
| 6,749,589 B1 | 6/2004 | Douglas et al. | 604/165.01 |
| 6,805,693 B2 | 10/2004 | Gray et al. | 604/891.1 |
| 6,840,922 B2 | 1/2005 | Nielsen et al. | 604/263 |
| 6,908,459 B2 | 6/2005 | Harding et al. | 604/533 |
| 6,960,192 B1 | 11/2005 | Flaherty et al. | 604/181 |
| 6,964,649 B2 | 11/2005 | Goll | 604/68 |
| 7,008,383 B1 | 3/2006 | Damadian et al. | 600/567 |
| 7,022,108 B2 | 4/2006 | Marano-Ford et al. | 604/157 |
| 7,029,455 B2 | 4/2006 | Flaherty | 604/131 |
| 7,033,339 B1 | 4/2006 | Lynn | 604/256 |
| 7,083,597 B2 | 8/2006 | Lynch et al. | 604/174 |
| 7,309,326 B2 * | 12/2007 | Fangrow, Jr. | 604/167.02 |
| 7,338,465 B2 | 3/2008 | Patton | 604/167.01 |
| 7,704,228 B2 * | 4/2010 | Patton | 604/93.01 |
| 7,892,216 B2 * | 2/2011 | Fangrow, Jr. | 604/288 |
| 7,931,615 B2 * | 4/2011 | Fangrow, Jr. | 604/93.01 |
| 8,226,614 B2 * | 7/2012 | Turner et al. | 604/164.04 |
| 2001/0053887 A1 | 12/2001 | Douglas et al. | 604/152 |
| 2001/0053889 A1 | 12/2001 | Marggi et al. | 604/164.11 |
| 2001/0056064 A1 | 12/2001 | Aoki | 514/4 |
| 2002/0045867 A1 | 4/2002 | Nielsen et al. | 604/263 |
| 2002/0065484 A1 | 5/2002 | Douglas et al. | 604/93.01 |
| 2002/0072720 A1 | 6/2002 | Hague et al. | 604/264 |
| 2002/0072733 A1 | 6/2002 | Flaherty | 604/890.1 |
| 2002/0107476 A1 | 8/2002 | Mann et al. | 604/67 |
| 2002/0120231 A1 | 8/2002 | Douglas et al. | 604/82 |
| 2002/0123719 A1 | 9/2002 | Lavi et al. | 604/82 |
| 2002/0123740 A1 * | 9/2002 | Flaherty et al. | 604/890.1 |
| 2002/0128600 A1 | 9/2002 | Nissels | 604/131 |
| 2002/0151855 A1 | 10/2002 | Douglas et al. | 604/218 |
| 2002/0161332 A1 | 10/2002 | Ramey | 604/164.07 |
| 2002/0173769 A1 | 11/2002 | Gray et al. | 604/506 |
| 2003/0023203 A1 | 1/2003 | Lavi et al. | 604/82 |
| 2003/0073952 A1 | 4/2003 | Flaherty et al. | 604/151 |
| 2003/0088238 A1 | 5/2003 | Poulsen et al. | 604/890.1 |
| 2003/0097092 A1 | 5/2003 | Flaherty | 604/67 |
| 2003/0100885 A1 | 5/2003 | Pettis et al. | 604/506 |
| 2003/0114751 A1 | 6/2003 | Pedain et al. | 600/431 |
| 2003/0199823 A1 | 10/2003 | Bobroff et al. | 604/136 |
| 2003/0212364 A1 | 11/2003 | Mann et al. | 604/131 |
| 2003/0213723 A1 | 11/2003 | Lombardi | 206/581 |
| 2003/0216686 A1 | 11/2003 | Lynch et al. | 604/93.01 |
| 2004/0001809 A1 | 1/2004 | Brisken et al. | 424/93.21 |
| 2004/0002682 A1 | 1/2004 | Kovelman et al. | 604/136 |
| 2004/0006316 A1 * | 1/2004 | Patton | 604/288.02 |
| 2004/0015134 A1 | 1/2004 | Lavi et al. | 604/183 |
| 2004/0030285 A1 | 2/2004 | Lavi et al. | 604/82 |
| 2004/0073160 A1 | 4/2004 | Pinkerton | 604/28 |
| 2004/0143216 A1 | 7/2004 | Douglas et al. | 604/116 |
| 2004/0143241 A1 | 7/2004 | Douglas et al. | 604/533 |
| 2004/0204687 A1 * | 10/2004 | Mogensen et al. | 604/181 |
| 2004/0204690 A1 | 10/2004 | Yashiro et al. | 604/257 |
| 2004/0204691 A1 | 10/2004 | Yashiro et al. | 604/257 |
| 2004/0260235 A1 | 12/2004 | Douglas | 604/93.01 |
| 2004/0267238 A1 | 12/2004 | Haarala et al. | 604/502 |
| 2005/0101910 A1 | 5/2005 | Bowman et al. | 604/93.01 |
| 2005/0101933 A1 | 5/2005 | Marrs et al. | 604/506 |
| 2005/0104473 A1 | 5/2005 | Yoshida | 310/309 |
| 2005/0107743 A1 | 5/2005 | Fangrow | 604/164.01 |
| 2005/0240154 A1 | 10/2005 | Mogensen et al. | 604/173 |
| 2006/0015076 A1 | 1/2006 | Heinzerling et al. | 604/264 |
| 2006/0030815 A1 | 2/2006 | Csincsura et al. | 604/93.01 |
| 2006/0129090 A1 | 6/2006 | Moberg et al. | 604/93.01 |
| 2006/0173386 A1 | 8/2006 | Lindquist | 601/2 |
| 2006/0217659 A1 | 9/2006 | Patton | 604/93.01 |
| 2006/0264818 A1 | 11/2006 | Patton | 604/93 |
| 2006/0264900 A1 | 11/2006 | Patton | 604/506 |
| 2006/0264901 A1 | 11/2006 | Patton | 604/506 |
| 2007/0049874 A1 | 3/2007 | Patton | 604/288.01 |
| 2007/0049875 A1 | 3/2007 | Patton | 604/288.01 |
| 2007/0049876 A1 | 3/2007 | Patton | 604/288.01 |
| 2007/0049877 A1 | 3/2007 | Patton | 604/288.01 |
| 2007/0088385 A1 | 4/2007 | Perry | 606/203 |
| 2007/0093756 A1 | 4/2007 | Patton | 604/167.01 |
| 2007/0093757 A1 | 4/2007 | Patton | 604/167.01 |

FOREIGN PATENT DOCUMENTS

| | | |
|---|---|---|
| EP | 1 205 211 A1 | 5/2002 |
| EP | 1566193 | 8/2005 |
| FR | 2607012 | 5/1988 |
| JP | 59-118152 | 7/1984 |
| JP | 03-126438 | 5/1991 |

(56) References Cited

FOREIGN PATENT DOCUMENTS

| WO | WO 87/01041 | 2/1987 |
|---|---|---|
| WO | WO 88/03816 | 6/1988 |
| WO | WO 92/20400 | 11/1992 |

OTHER PUBLICATIONS

Dyer et al., "Insuflon Versus Subcutaneous Injection for Cytokine Administration in Children for Cytokine Administration in Children and Adolescents: A Randomized Crossover Study," *J. Pediatric Oncology Nursing*, 21:79-86, 2004.

Graham et al., "Control of Important Clinical Parameters for Patients with Type 2 Diabetes Mellitus," *Diabetes*, 51:A-274, 2002 (Abstract No. 1112-P).

Hanas, "Reducing injection pain in children and adolescents with diabetes: a review of indwelling catheters," *Pediatric Diabetes*, 5:102, 2004.

Heine, "A Randomized trial of continuous subcutaneous insulin infusion and intensive injection therapy in type 1 diabetes for patients with long-standing poor glycemic control," *Diabetes Care*, Nov. 1, 2002.

Kaar et al., "Insulin Administration via a Subcutaneous Catheter: Effects on absorption," *Diabetes Care*, 16:1412-1413, 1993.

Koro et al., "Glycemic control from 1988 to 2000 among U.S. adults diagnosed with type 2 diabetes: a preliminary report," *Diabetes Care*, 27:17-20, 2004.

Su et al., "The Relationship between Regimen Burden and Psychological Well Being in Persons with Type 1 Diabetes: Inhaled vs Injectable Insulin," *American Diabetes Association 62nd Annual Meeting and Scientific Sessions*, San Francisco, CA, Jun. 14-18, 2002 (Abstract No. 1843-P, p. A448).

Taddio et al., "Use of lidocaine-priolcaine cream for vaccination pain in infants," *J. Pediatr.*, 124:643-648, 1994.

"Insuflon" retrieved on Nov. 12, 2004 from http://www.poara.com/eng/insuflon/insuflon.htm.

American Diabetes Association "Standards of medical care for patients with diabetes mellitus." *Diabetes Care*, 25:213-29, 2002.

Anderson DR, et al. "The use of an indwelling Teflon catheter for subcutaneous heparin administration during pregnancy. A randomized crossover study." *Arch. Intern. Med.*, 153:841-4, 1993.

FDA, Section 510(k) Notification for Viggo Insuflon, Aug. 24, 1998, Silver Spring, Maryland.

File History of U.S. Appl. No. 09/110,360 filed Jul. 6, 1998.

Hanas R, et al. "Side effects and indwelling times of subcutaneous catheters for insulin injections: a new device for injecting insulin with a minimum of pain in the treatment of insulin-dependent diabetes mellitus." *Diabetes Res. Clin. Pract.*, 10:73-83, 1990.

Hanas SR, et al. "Metabolic control is not altered when using indwelling catheters for insulin injections." *Diabetes Care*, 17:716-8, 1994.

Hanas SR, et al. "Unchanged insulin absorption after 4 days' use of subcutaneous indwelling catheters for insulin injections." *Diabetes Care*, 20:487-90, 1997.

Hanas, R. et al. "Experience of Pain from Insulin Injections Using Syringes Pens and Indwelling Catheters." Department of Pediatrics, Uddevalla Hospital, Uddevalla Sweden. Abstract. 1989.

Hanas, Ragnar et al. "X-ray appearance of the indwelling catheter when using insuflon for insulin injections." Department of Pediatrics Uddevalla Hospital, Uddevalla, Sweden. Abstracts of the 17th Annual Meeting of ISGD, Hormone Research 35:58, 1991.

Henry RR, et al. "Intensive conventional insulin therapy for type II diabetes. Metabolic effects during a 6-mo outpatient trial." *Diabetes Care*, 16:21-31, 1993.

Hunt LM, et al. "NIDDM patients' fears and hopes about insulin therapy. The basis of patient reluctance." *Diabetes Care*, 20:292-8, 1997.

Knip, Mikael et al. "No evidence of an accelerated absorption of exogenous insulin after using a subcutaneous catheter for 5 days in children with IDDM" *Diabetes Care*, June, 17:627, 1994.

Lamacraft G, et al. "Subcutaneous cannulae for morphine boluses in children: assessment of a technique," *J. Pain Symptom Manage.*, 13:43-9, 1997.

Liu D, et al. "Insulin absorption is faster when keeping the infusion site in use for three days during continuous subcutaneous insulin infusion." *Diabetes Res. Clin. Pract.*, 12:19-24, 1991.

Long AM, et al. "Indwelling cannula for insulin administration in diabetes mellitus." *Arch. Dis. Child*, 66:348-9, 1991.

McGrath PA, et al. "A new analogue scale for assessing children's pain: an initial validation study," *Pain*, Mar; 64:435-43, 1996.

Selam JL, et al. "Devices for insulin administration." *Diabetes Care*, 13:955-79, 1990.

Testa, Marcia A. et al. "Patient satisfaction with insulin therapy in type 2 diabetes: a randomized trial of injectable vs. inhaled insulin." *American Diabetes Association 62nd Annual Meeting and Scientific Sessions*, Jun. 14-18, 2002, San Francisco, CA, US.

Zambanini A, et al. "Injection related anxiety in insulin-treated diabetes." *Diabetes Res. Clin. Pract.*, 46:239-46, 1999.

English Translation of Office Action issued in Chinese Application No. 038158213, mailed Jul. 6, 2007.

English Translation of Office Action issued in Chinese Application No. 038158213, mailed Feb. 20, 2009.

English Translation of Office Action issued in Chinese Patent App. No. 03815821.3, mailed Jun. 26, 2009.

English Translation of Office Action issued in Japanese Application No. 2004-519654, mailed Apr. 28, 2008.

English Translation of Office Action issued in Japanese Application No. 2004-519654, mailed Nov. 25, 2008.

Notice of Allowance, issued in U.S. Appl. No. 11/483,218, mailed Oct. 7, 2008.

Notice of Allowance, issued in U.S. Appl. No. 11/483,218, mailed Feb. 10, 2009.

Office Action, issued in U.S. Appl. No. 11/372,681, mailed Aug. 25, 2006.

Office Action, issued in U.S. Appl. No. 11/372,681, mailed Feb. 23, 2007.

Office Action, issued in U.S. Appl. No. 11/372,681, mailed Aug. 24, 2007.

Office Action, issued in U.S. Appl. No. 11/372,681, mailed Dec. 27, 2007.

Office Action, issued in U.S. Appl. No. 11/372,681, mailed May 1, 2008.

Office Action, issued in U.S. Appl. No. 11/372,681, mailed Sep. 12, 2008.

Office Action, issued in U.S. Appl. No. 11/372,681, mailed Feb. 20, 2009.

Office Action, issued in U.S. Appl. No. 11/372,681, mailed Aug. 6, 2009.

Office Action, issued in U.S. Appl. No. 11/482,265, mailed Aug. 25, 2006.

Office Action, issued in U.S. Appl. No. 11/482,265, mailed Nov. 30, 2006.

Office Action, issued in U.S. Appl. No. 11/482,265, mailed May 30, 2007.

Office Action, issued in U.S. Appl. No. 11/482,265, mailed Dec. 11, 2007.

Office Action, issued in U.S. Appl. No. 11/482,265, mailed Apr. 3, 2008.

Office Action, issued in U.S. Appl. No. 11/482,265, mailed Jan. 12, 2009.

Office Action, issued in U.S. Appl. No. 11/482,265, mailed May 29, 2009.

Office Action, issued in U.S. Appl. No. 11/483,218, mailed Aug. 25, 2006.

Office Action, issued in U.S. Appl. No. 11/483,218, mailed Nov. 30, 2006.

Office Action, issued in U.S. Appl. No. 11/483,218, mailed Mar. 26, 2007.

Office Action, issued in U.S. Appl. No. 11/483,218, mailed Jul. 27, 2007.

Office Action, issued in U.S. Appl. No. 11/483,218, mailed Apr. 8, 2008.

(56) References Cited

OTHER PUBLICATIONS

Office Action, issued in U.S. Appl. No. 11/483,219, mailed Aug. 11, 2006.
Office Action, issued in U.S. Appl. No. 11/483,219, mailed Nov. 30, 2006.
Office Action, issued in U.S. Appl. No. 11/483,219, mailed May 30, 2007.
Office Action, issued in U.S. Appl. No. 11/483,219, mailed Dec. 11, 2007.
Office Action, issued in U.S. Appl. No. 11/483,219, mailed Apr. 3, 2008.
Office Action, issued in U.S. Appl. No. 11/483,219, mailed Jan. 12, 2009.
Office Action, issued in U.S. Appl. No. 11/483,219, mailed May 29, 2009.
Office Action, issued in U.S. Appl. No. 11/532,747, mailed Dec. 27, 2007.
Office Action, issued in U.S. Appl. No. 11/532,747, mailed Jun. 30, 2008.
Office Action, issued in U.S. Appl. No. 11/532,747, mailed Oct. 8, 2008.
Office Action, issued in U.S. Appl. No. 11/532,747, mailed Mar. 18, 2009.
Office Action, issued in U.S. Appl. No. 11/532,772, mailed Nov. 12, 2008.
Office Action, issued in U.S. Appl. No. 11/532,772, mailed Jun. 2, 2009.
Office Action, issued in U.S. Appl. No. 11/532,824, mailed Apr. 1, 2009.
Office Action, issued in U.S. Appl. No. 11/532,836, mailed Jan. 29, 2008.
Office Action, issued in U.S. Appl. No. 11/532,836, mailed Jun. 27, 2008.
Office Action, issued in U.S. Appl. No. 11/532,836, mailed Sep. 17, 2008.
Office Action, issued in U.S. Appl. No. 11/532,836, mailed Feb. 20, 2009.
Office Action, issued in U.S. Appl. No. 11/532,836, mailed Aug. 6, 2009.
Office Action, issued in U.S. Appl. No. 11/532,845, mailed Apr. 9, 2009.
Office Action, issued in U.S. Appl. No. 11/532,858, mailed Apr. 9, 2009.
Response to Office Action, in U.S. Appl. No. 11/372,681, dated Nov. 27, 2006.
Response to Office Action, in U.S. Appl. No. 11/372,681, dated Jun. 25, 2007.
Response to Office Action, in U.S. Appl. No. 11/372,681, dated Nov. 26, 2007.
Response to Office Action, in U.S. Appl. No. 11/372,681, dated Mar. 20, 2008.
Response to Office Action, in U.S. Appl. No. 11/372,681, dated Aug. 1, 2008.
Response to Office Action, in U.S. Appl. No. 11/372,681, dated Dec. 18, 2008.
Response to Office Action, in U.S. Appl. No. 11/372,681, dated May 20, 2009.
Response to Office Action, in U.S. Appl. No. 11/372,681, dated Sep. 8, 2009.
Response to Office Action, in U.S. Appl. No. 11/482,265, dated Sep. 15, 2006.
Response to Office Action, in U.S. Appl. No. 11/482,265, dated Feb. 28, 2007.
Response to Office Action, in U.S. Appl. No. 11/482,265, dated Sep. 12, 2007.
Response to Office Action, in U.S. Appl. No. 11/482,265, dated Mar. 20, 2008.
Response to Office Action, in U.S. Appl. No. 11/482,265, dated Oct. 3, 2008.
Response to Office Action, in U.S. Appl. No. 11/482,265, dated Apr. 13, 2009.
Response to Office Action, in U.S. Appl. No. 11/482,265, dated Aug. 31, 2009.
Response to Office Action, in U.S. Appl. No. 11/483,218, dated Sep. 15, 2006.
Response to Office Action, in U.S. Appl. No. 11/483,218, dated Feb. 28, 2007.
Response to Office Action, in U.S. Appl. No. 11/483,218, dated May 10, 2007.
Response to Office Action, in U.S. Appl. No. 11/483,218, dated Jan. 6, 2008.
Response to Office Action, in U.S. Appl. No. 11/483,218, dated Aug. 4, 2008.
Response to Office Action, in U.S. Appl. No. 11/483,219, dated Sep. 15, 2006.
Response to Office Action, in U.S. Appl. No. 11/483,219, dated Feb. 28, 2007.
Response to Office Action, in U.S. Appl. No. 11/483,219, dated Sep. 12, 2007.
Response to Office Action, in U.S. Appl. No. 11/483,219, dated Mar. 20, 2008.
Response to Office Action, in U.S. Appl. No. 11/483,219, dated Oct. 3, 2008.
Response to Office Action, in U.S. Appl. No. 11/483,219, dated Apr. 13, 2009.
Response to Office Action, in U.S. Appl. No. 11/483,219, dated Aug. 31, 2009.
Response to Office Action, in U.S. Appl. No. 11/532,747, dated Mar. 20, 2008.
Response to Office Action, in U.S. Appl. No. 11/532,747, dated Aug. 4, 2008.
Response to Office Action, in U.S. Appl. No. 11/532,747, dated Mar. 9, 2009.
Response to Office Action, in U.S. Appl. No. 11/532,747, dated Jul. 17, 2009.
Response to Office Action, in U.S. Appl. No. 11/532,772, dated Mar. 12, 2009.
Response to Office Action, in U.S. Appl. No. 11/532,772, dated Sep. 8, 2009.
Response to Office Action, in U.S. Appl. No. 11/532,824, dated Jul. 1, 2009.
Response to Office Action, in U.S. Appl. No. 11/532,836, dated Mar. 20, 2008.
Response to Office Action, in U.S. Appl. No. 11/532,836, dated Aug. 4, 2008.
Response to Office Action, in U.S. Appl. No. 11/532,836, dated Dec. 17, 2008.
Response to Office Action, in U.S. Appl. No. 11/532,836, dated May 20, 2009.
Response to Office Action, in U.S. Appl. No. 11/532,836, dated Sep. 8, 2009.
Response to Office Action, in U.S. Appl. No. 11/532,845, dated Jul. 9, 2009.
Response to Office Action, in U.S. Appl. No. 11/532,858, dated Jul. 9, 2009.
Text of Office Action, in Japanese App. No. 2004-519654, mailed Oct. 16, 2009. (English translation).
Office Action, in U.S. Appl. No. 10/188,591, mailed Dec. 15, 2005.
Office Action, in U.S. Appl. No. 10/188,591, mailed Feb. 27, 2006.
Office Action, in U.S. Appl. No. 10/188,591, mailed Jun. 7, 2006.
Office Action, in U.S. Appl. No. 10/188,591, mailed Sep. 20, 2006.
Office Action, in U.S. Appl. No. 10/188,591, mailed Dec. 15, 2006.
Office Action, in U.S. Appl. No. 10/188,591, mailed May 30, 2007.
Office Action, in U.S. Appl. No. 11/372,681, mailed Nov. 20, 2009.
Office Action, in U.S. Appl. No. 11/466,349, mailed Jun. 12, 2009.
Office Action, in U.S. Appl. No. 11/466,349, mailed Nov. 6, 2009.
Office Action, in U.S. Appl. No. 11/482,265, mailed Nov. 17, 2009.
Office Action, in U.S. Appl. No. 11/483,219, mailed Nov. 17, 2009.
Office Action, in U.S. Appl. No. 11/532,747, mailed Oct. 21, 2009.
Office Action, in U.S. Appl. No. 11/532,772, mailed Oct. 23, 2009.
Office Action, in U.S. Appl. No. 11/532,824, mailed Oct. 22, 2009.
Office Action, in U.S. Appl. No. 11/532,836, mailed Nov. 19, 2009.

(56) References Cited

OTHER PUBLICATIONS

Office Action, in U.S. Appl. No. 11/532,845, mailed Oct. 30, 2009.
Office Action, in U.S. Appl. No. 11/532,858, mailed Oct. 30, 2009.
Response to Office Action, in U.S. Appl. No. 10/188,591, dated Jan. 17, 2006.
Response to Office Action, in U.S. Appl. No. 10/188,591, dated Mar. 9, 2006.
Response to Office Action, in U.S. Appl. No. 10/188,591, dated Sep. 1, 2006.
Response to Office Action, in U.S. Appl. No. 10/188,591, dated Sep. 26, 2006.
Response to Office Action, in U.S. Appl. No. 10/188,591, dated Mar. 15, 2007.
Response to Office Action, in U.S. Appl. No. 10/188,591, dated Sep. 28, 2007.
Response to Office Action, in U.S. Appl. No. 11/466,349, dated Sep. 14, 2009.
Response to Office Action, in U.S. Appl. No. 11/483,218, dated Jan. 7, 2009.
Response to Office Action, in U.S. Appl. No. 11/532,858, dated Dec. 17, 2008.
Response to Office Action, in U.S. Appl. No. 11/532,858, dated Feb. 1, 2010.
Response to Office Action, in U.S. Appl. No. 11/532,845, dated Feb. 1, 2010.
Response to Office Action in U.S. Appl. No. 11/532,747, dated Mar. 22, 2010.
Office Action in U.S. Appl. No. 11/532,747, dated Mar. 31, 2010.
Response to Office Action in U.S. Appl. No. 11/532,747, dated Sep. 30, 2010.
Office Action in U.S. Appl. No. 11/532,747, dated Nov. 17, 2011.
Response to Office Action in U.S. Appl. No. 11/532,747, dated Apr. 12, 2011.
Response to Office Action in U.S. Appl. No. 11/532,772, dated Mar. 23, 2010.
Office Action in U.S. Appl. No. 11/532,772, dated Apr. 28, 2010.
Response to Office Action in U.S. Appl. No. 11/532,772, dated Oct. 28, 2010.
Office Action in U.S. Appl. No. 11/532,772, dated Jan. 12, 2011.
Response to Office Action in U.S. Appl. No. 11/532,772, dated Apr. 11, 2011.
Response to Office Action in U.S. Appl. No. 11/532,824, dated Mar. 22, 2010.
Office Action in U.S. Appl. No. 11/532,824, dated May 12, 2010.
Response to Office Action in U.S. Appl. No. 11/532,824, dated Oct. 12, 2010.
Response to Office Action in U.S. Appl. No. 11/532,836, dated Apr. 19, 2010.
Office Action in U.S. Appl. No. 11/532,836, dated May 20, 2010.
Response to Office Action in U.S. Appl. No. 11/532,836, dated Nov. 22, 2010.
Office Action in U.S. Appl. No. 11/532,836, dated Jan. 11, 2011.
Response to Office Action in U.S. Appl. No. 11/532,836, dated Apr. 12, 2011.
Office Action in U.S. Appl. No. 12/042,206, dated Sep. 20, 2010.
Response to Office Action in U.S. Appl. No. 12/042,206, dated Jan. 20, 2011.
Office Action in U.S. Appl. No. 12/042,206, dated Mar. 23, 2011.
Office Action in U.S. Appl. No. 12/042,212, dated Jan. 18, 2011.
Response to Office Action in U.S. Appl. No. 12/042,212, dated Apr. 18, 2011.
Response to Office Action in U.S. Appl. No. 11/372,681, dated Mar. 22, 2010.
Office Action in U.S. Appl. No. 11/372,681, dated May 6, 2010.
Response to Office Action in U.S. Appl. No. 11/372,681, dated Nov. 5, 2010.
Office Action in U.S. Appl. No. 11/372,681, dated Dec. 16, 2010.
Response to Office Action in U.S. Appl. No. 11/372,681, dated Apr. 12, 2011.
Response to Office Action in U.S. Appl. No. 11/483,219, dated Apr. 19, 2010.
Office Action in U.S. Appl. No. 11/483,219, dated Jun. 9, 2010.
Response to Office Action in U.S. Appl. No. 11/483,219, dated Nov. 9, 2010.
Office Action in U.S. Appl. No. 11/483,219, dated Dec. 16, 2010.
Response to Office Action in U.S. Appl. No. 11/483,219, dated Apr. 12, 2011.
Response to Office Action in U.S. Appl. No. 11/482,265, dated Apr. 19, 2010.
Office Action in U.S. Appl. No. 11/482,265, dated Jun. 10, 2010.
Response to Office Action in U.S. Appl. No. 11/482,265, dated Nov. 9, 2010.
Office Action in U.S. Appl. No. 11/482,265, dated Dec. 16, 2010.
Response to Office Action in U.S. Appl. No. 11/482,265, dated Apr. 12, 2011.
Office Action in Chinese Patent Application No. 200680038075.2, dated Nov. 23, 2010.
Office Action in Russian Patent Application No. 2008110940/14, dated Jun. 11, 2010.
Office Action in U.S. Appl. No. 11/592,719, dated Oct. 18, 2010.
Office Action in U.S. Appl. No. 11/592,719, dated Nov. 18, 2010.
Office Action in U.S. Appl. No. 11/592,719, dated Dec. 10, 2010.
Response to Office Action in U.S. Appl. No. 11/592,719, dated Apr. 11, 2011.
Office Action in Canadian Patent Application No. 2,490,549, dated Dec. 20, 2010.
Office Action in U.S. Appl. No. 11/466,219, dated May 4, 2011.
Office Action in U.S. Appl. No. 11/592,719, dated Jun. 1, 2011.
Office Action issued in Chinese Application No. 2006800475377, dated Oct. 29, 2010.
Office Action issued in New Zealand Patent Application No. 566773, dated Oct. 9, 2009.
Office Action issued in New Zealand Patent Application No. 567891, dated Nov. 9, 2009.
Office Action issued in Russian Patent Application No. 2008122063, dated Oct. 5, 2010.

* cited by examiner

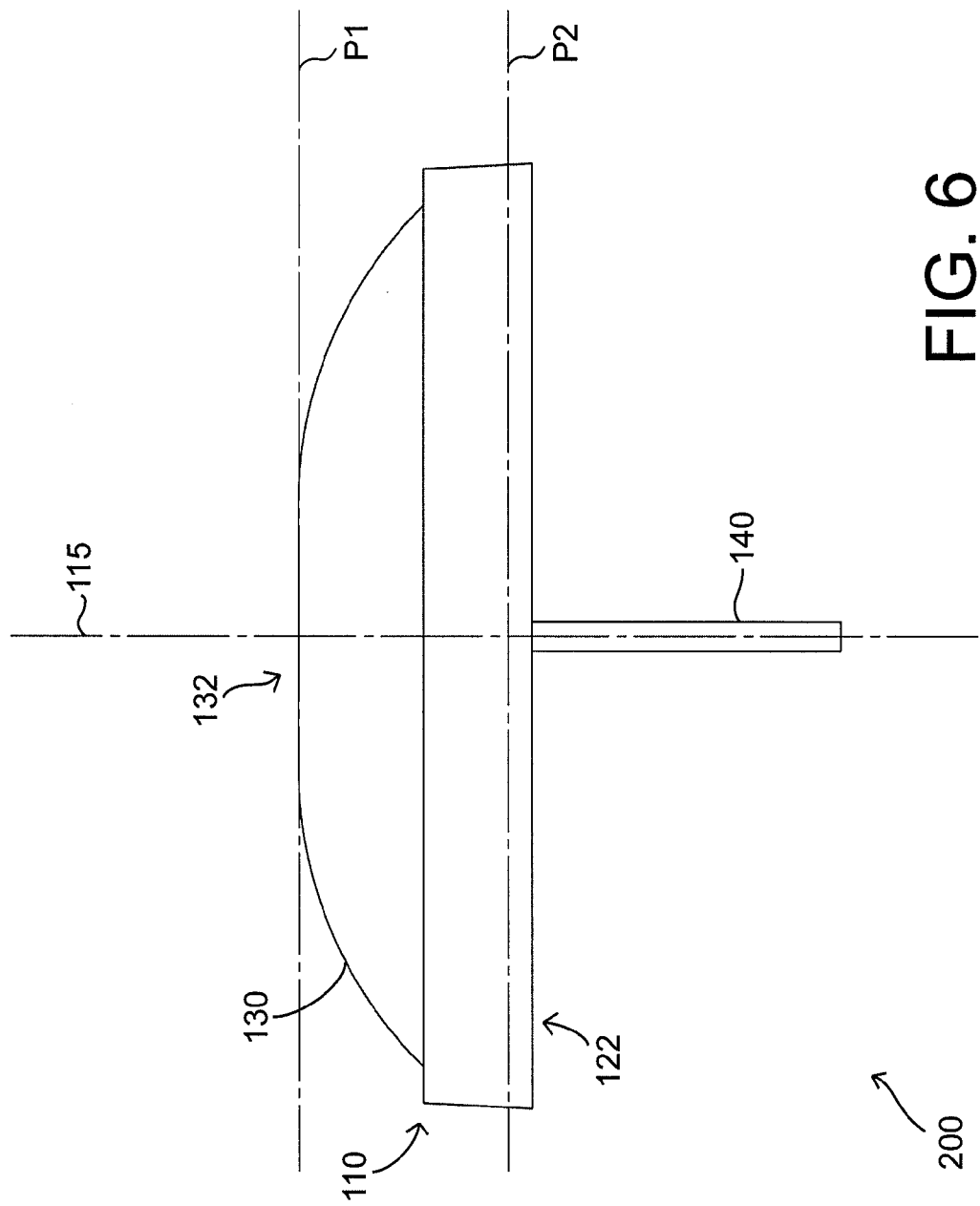

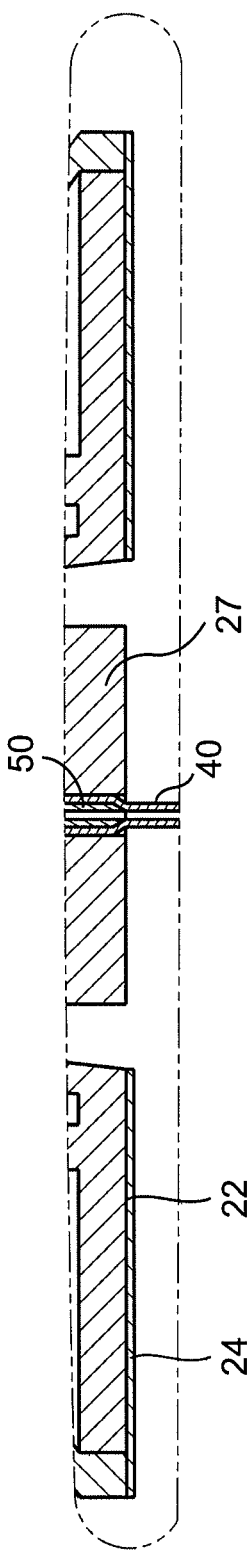
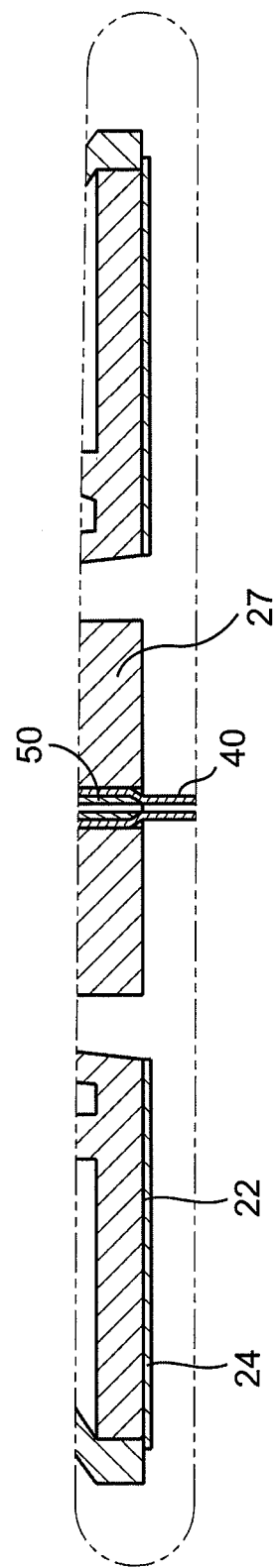
FIG. 8A
FIG. 8B

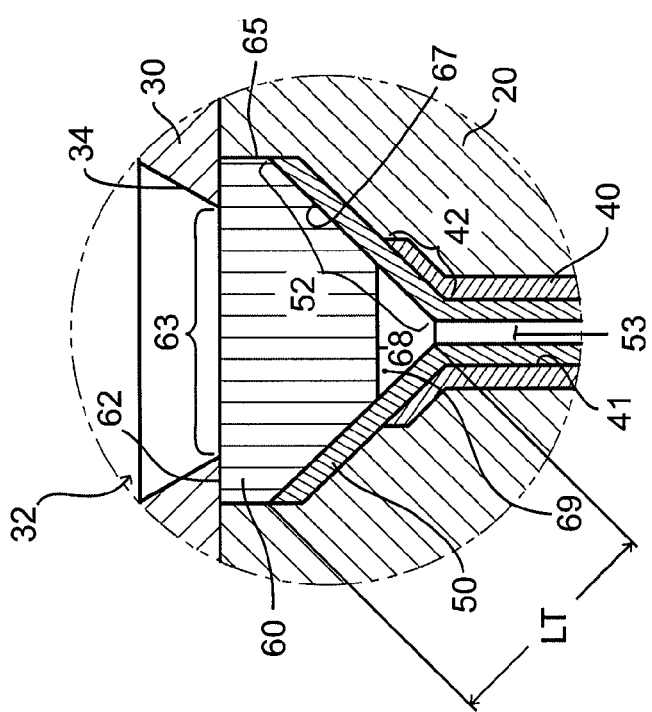
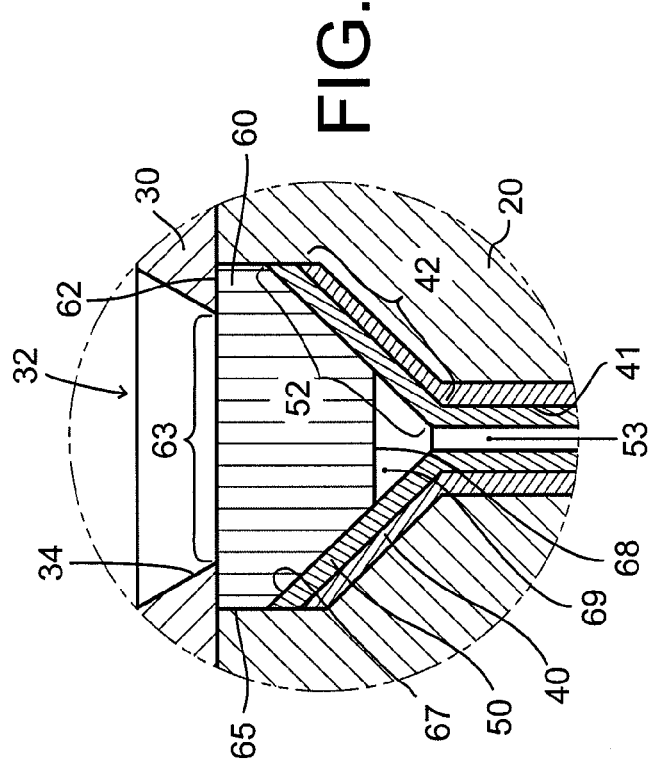

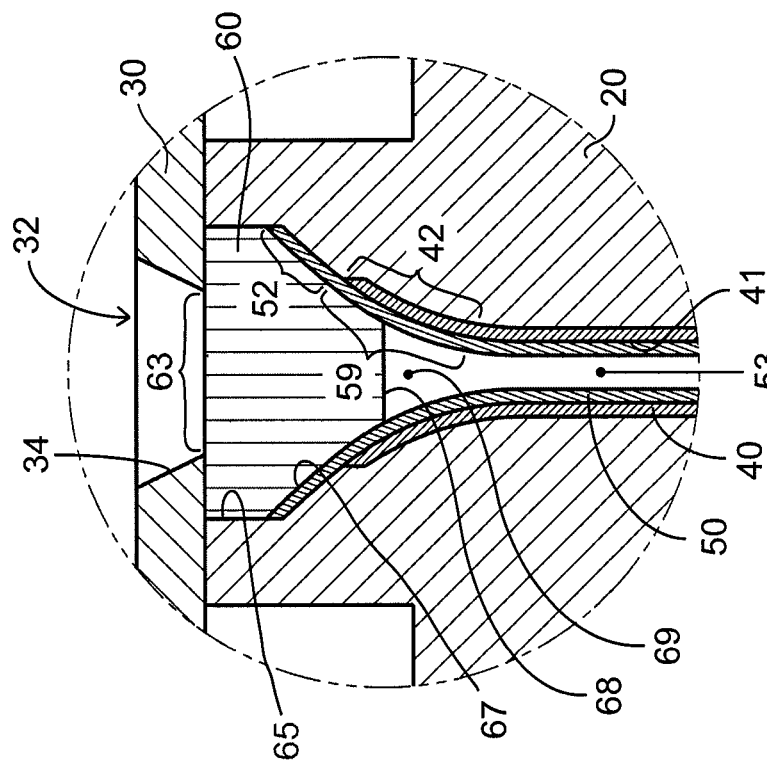

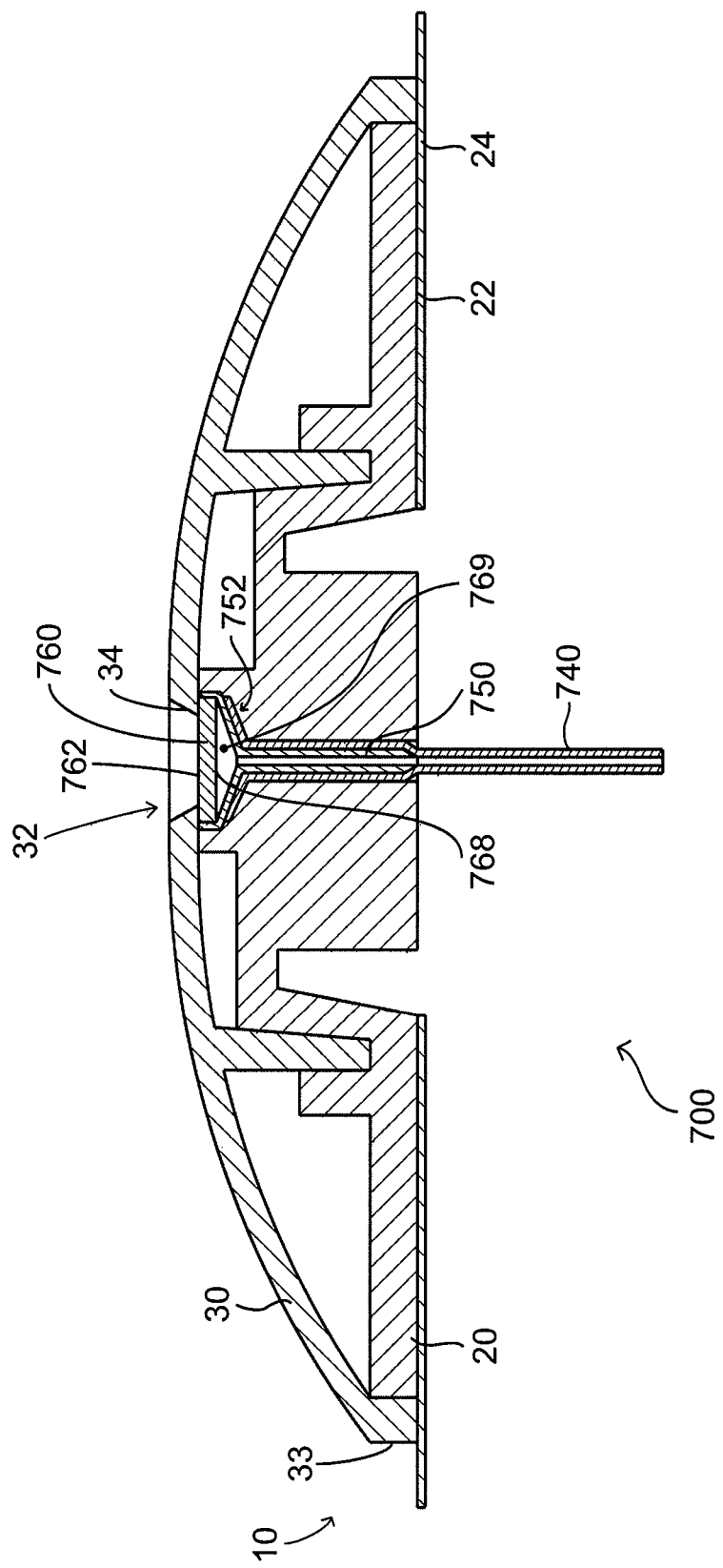

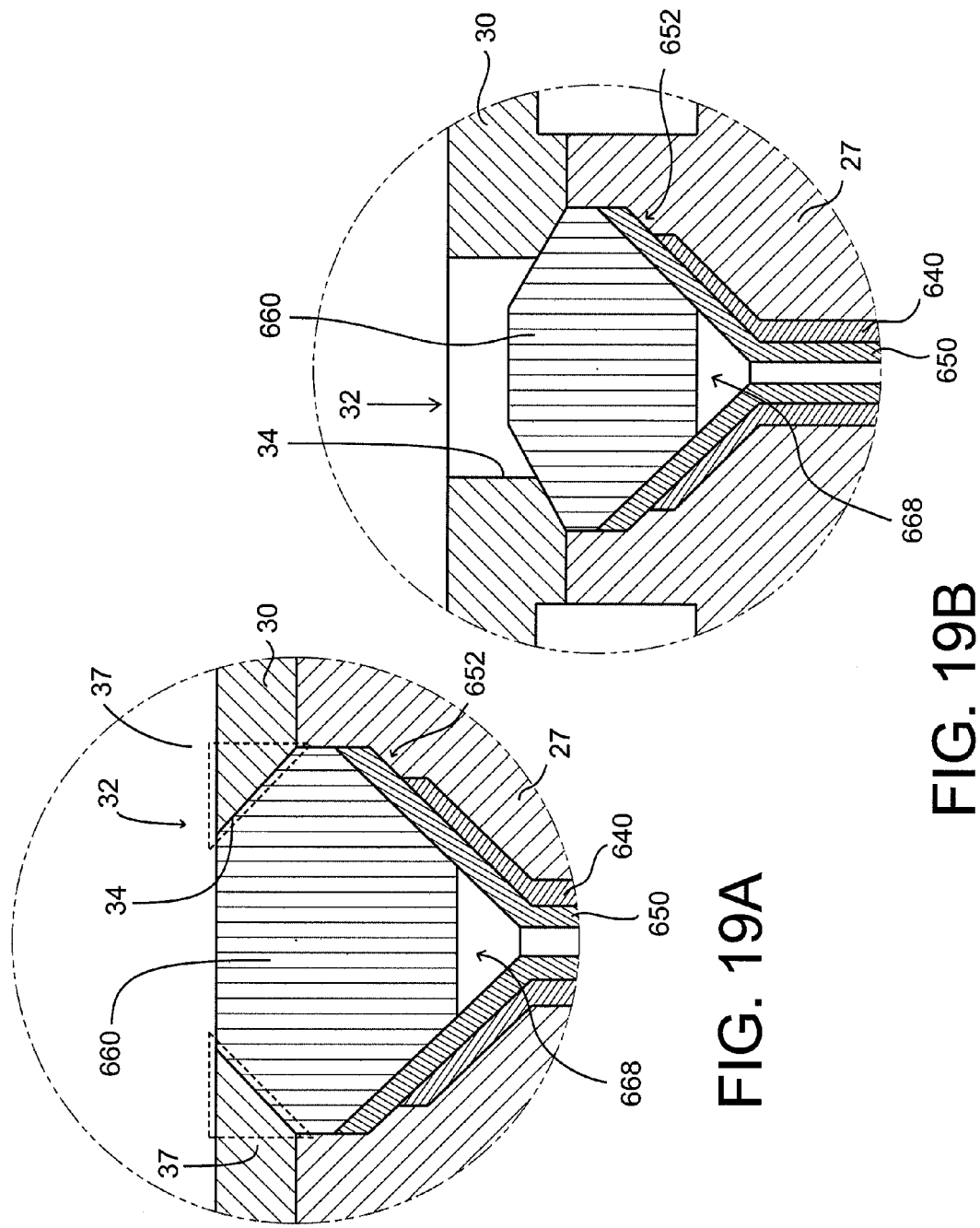

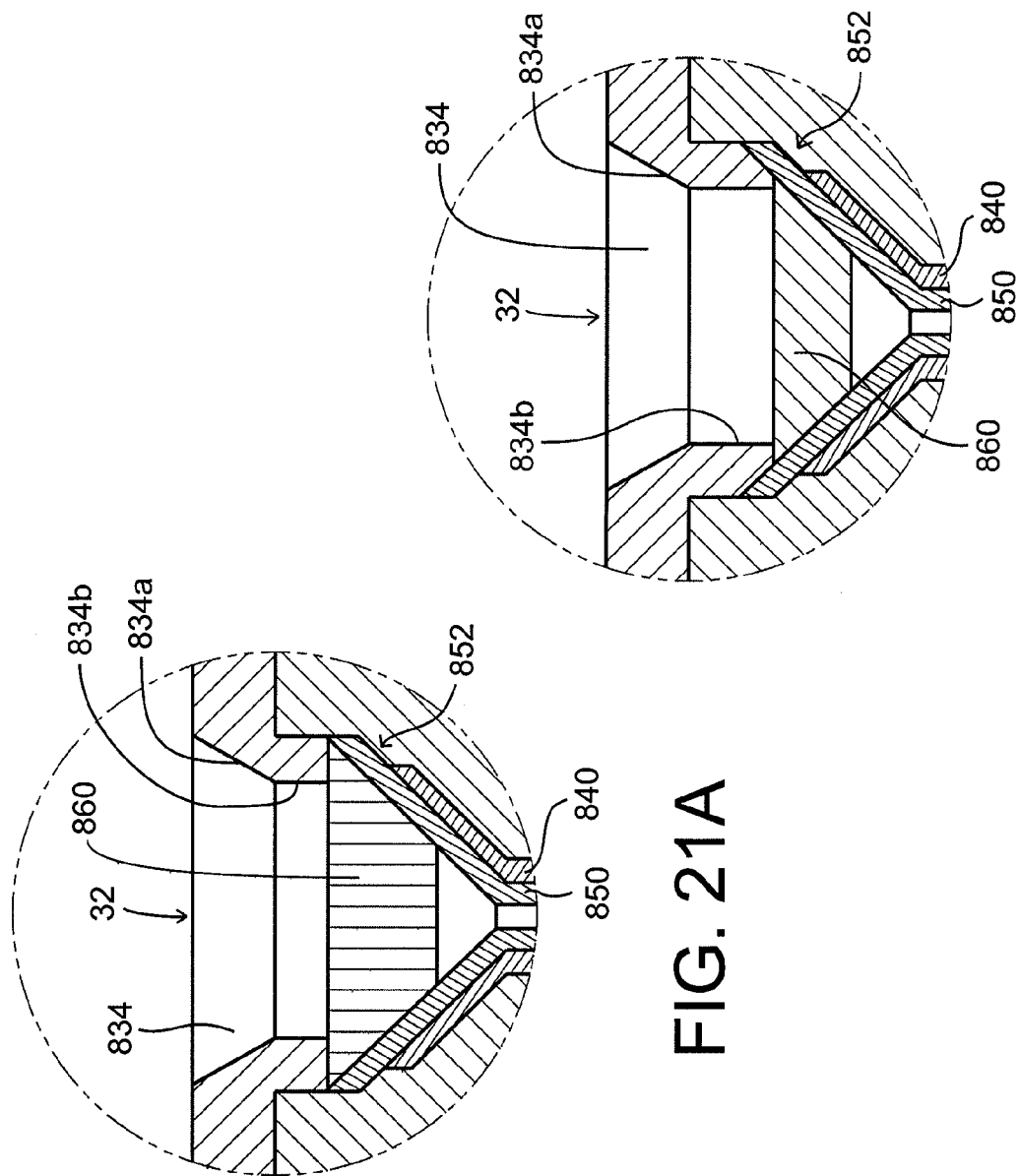

FLUID DELIVERY DEVICES, SYSTEMS AND METHODS

CROSS-REFERENCE(S) TO RELATED APPLICATION(S)

This application claims priority to U.S. Provisional Patent Application Ser. No. 60/710,315 filed Aug. 22, 2005. This provisional application is expressly incorporated by reference.

BACKGROUND OF THE INVENTION

1. Field of the Invention

The invention relates generally to devices that can be inserted in and attached to a living being for the purpose of facilitating the introduction of a fluid, such as medicine, into the living being. The invention also relates to systems that include one or more such devices, and to methods of delivering fluid into a living being.

2. Description of Related Art

Examples of devices that can be used to deliver fluids to a living being include: U.S. Pat. Nos. 4,755,173; 4,966,588; 5,968,011; 6,017,328; 6,056,718; 6,074,371; 6,685,674; 6,736,797; U.S. Patent Application Pub. Nos. 2002/0072720; 2004/0006316; 2005/0101910; 2005/0107743; and abandoned Ser. No. 09/110,360 (incorporated by reference in U.S. Pat. No. 6,074,371).

SUMMARY OF THE INVENTION

Some embodiments of the present fluid delivery devices, systems and methods may be used to deliver fluid such as insulin to users such as persons with diabetes. Some embodiments of the present fluid delivery devices may be configured to be worn for an extended period of time (e.g., multiple days) and allow a user to inject a fluid (such as a physician-prescribed medication) into the user's body without the need to repeatedly puncture the user's skin with a needle. The present fluid delivery devices, systems and methods include many different features that distinguish them from prior devices, and certain of those features are different in many ways from the features of prior devices. Different embodiments of the present fluid delivery devices, systems and methods include one or more of these features, which are interchangeable between embodiments to the extent that they are not inconsistent with the other features of a given embodiment.

Some embodiments of the present fluid delivery devices include, broadly, a body, a cannula, a needle guide, and a septum. The body may be made from one or more pieces, such as two pieces. The fluid delivery devices also may include an insertion device, such as an insertion hub to which an insertion needle is attached. The cannula may be a soft cannula.

Other embodiments of the present fluid delivery devices include, broadly, a body, a rigid cannula configured to pierce the skin of a user, and a septum.

Some embodiments of the present systems (which may be characterized as fluid delivery systems) include one or more of the present fluid delivery devices that have been sterilized and enclosed in a package, with or without instructions for use contained within the package. Some embodiments of the present systems also may include an injection device, such as a syringe.

Some embodiments of the present methods (which may be characterized as fluid delivery methods) include installing one of the present fluid delivery devices to a user, and delivering fluid through the device and into the user. The methods may involve delivering fluid from a non-pump source, and may involve delivering fluid to a user without using a fluid delivery line that is positioned completely outside of the user and at least partially outside of the body of the fluid delivery device.

BRIEF DESCRIPTION OF THE DRAWINGS

The following drawings illustrate by way of example and not limitation. Identical reference numbers do not necessarily indicate an identical structure. Rather, the same reference number may be used to indicate a similar feature or a feature with similar functionality, as may non-identical reference numbers. Every feature of each embodiment is not always labeled in every figure in which that embodiment appears, in order to keep the figures clear. The figures are drawn to scale, meaning the sizes of the depicted elements are accurate relative to each other for at least one set of embodiments of the present fluid delivery devices.

FIG. 6 is a front view of the arrangement shown in FIG. 5.

FIGS. 8A and 8B show different configurations of the adhesive layer shown in FIG. 7A.

FIGS. 9A-9C are enlarged detail views showing different configurations of the portion of the fluid delivery device shown in FIG. 7A that includes, and is located around, the septum.

FIGS. 14-17 are cross-sectional views showing different embodiments of septum, cannula, needle guide, and cap configurations of some embodiments of the present fluid delivery devices.

FIGS. 19A and 19B are enlarged detail views showing different configurations of the portion of the fluid delivery device shown in FIG. 16 that includes, and is located around, the septum.

FIGS. 21A and 21B are enlarged detail views of examples of different embodiments of the upper portion, including and surrounding a septum, of the present fluid delivery devices.

DESCRIPTION OF ILLUSTRATIVE EMBODIMENTS

Figure 1:
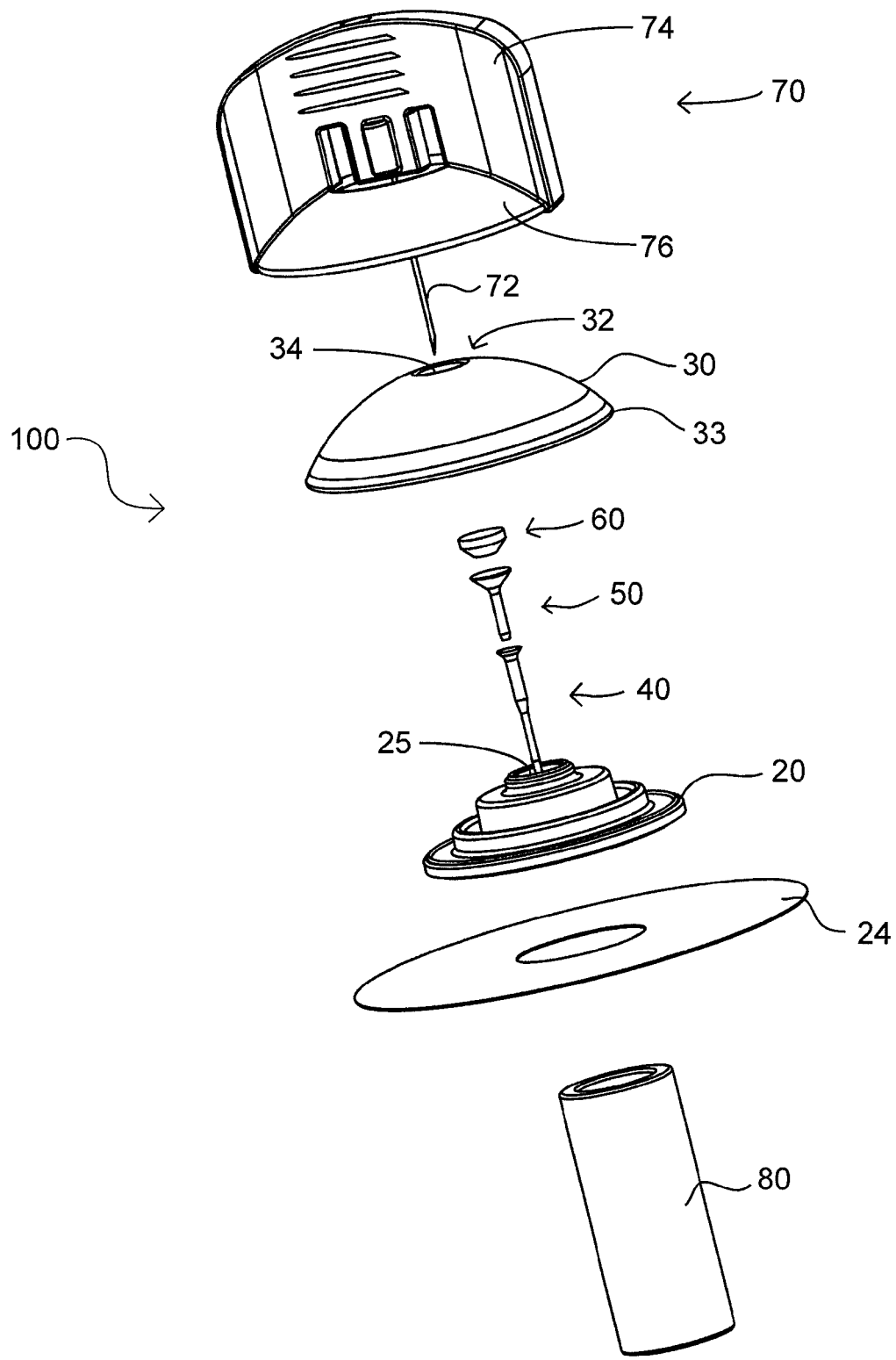
FIG. 1 is a perspective exploded view of one embodiment of the present fluid delivery devices.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device, a system or a method that "comprises," "has," "contains," or "includes" one or more recited elements or steps possesses those recited elements or steps, but is not limited to possessing only those elements or steps; it may possess elements or steps that are not recited. Likewise, an element of a device, system or method that "comprises," "has," "contains," or "includes" one or more recited features possesses those features, but is not limited to possessing only those features; it may possess features that are not recited. Furthermore, a structure that is configured in a certain way must be configured in at least that way, but also may be configured in a way or ways that are not specified.

Thus, and by way of example, a fluid delivery device comprising a body having a body passageway, a top, a bottom surface, a first perimeter at the top, and a second perimeter close to the bottom surface, the first perimeter being positioned in a first plane that is perpendicular to an axis that is parallel to a portion of the body passageway, the second perimeter being positioned in a second plane that is parallel to the first plane, and the second perimeter being greater than the first perimeter; a cannula having a cannula passageway and a portion extending from the bottom surface; a needle guide having a portion positioned within the cannula passageway; and a septum having a portion positioned within the needle guide, the septum having a middle in close contact with a surrounding portion of the fluid delivery device; the fluid delivery device being configured to adhere (e.g., directly) to a living being's skin, possesses the recited body, cannula, needle guide and septum, but is not limited to only possessing the recited elements (thus, other non-recited elements are not excluded). For example, the fluid delivery device also may include an insertion device. Furthermore, the elements recited are not limited to possessing only the recited features. For example, the septum may have a flat top surface and/or be wider than it is long.

In any of the claims, the term "consisting of" or "consisting essentially of" may be substituted for any of the open-ended linking verbs recited above, in order to change the scope of a given claim from what it would otherwise be using the open-ended linking verb.

The terms "a" and "an" are defined as one or more than one unless this disclosure explicitly requires otherwise. The term "substantially" is defined as at least close to (and includes) a given value or state (preferably within 10% of, more preferably within 1% of, and most preferably within 0.1% of). The term "close" is defined as near in relationship, considering the relative sizes of the elements/features that are close to each other.

Some embodiments of the present fluid delivery devices include, generally, a body, a cannula, and a septum. If the cannula is soft, these embodiments also include a needle guide, which also may be characterized as a cannula shield, that may be positioned inside a portion of the cannula in order to protect the cannula from inadvertent contact with an injection device (e.g., a needle) during fluid delivery. The present fluid delivery devices may be used to deliver fluid to a living being for any of a variety of reasons. For example, some embodiments of the present fluid delivery devices may be used to deliver insulin to the subcutaneous tissue of a person with diabetes. However, embodiments of the present fluid delivery devices also may be used to deliver other fluids, such as saline, medication other than insulin, chemicals, enzymes, antigens, hormones, vitamins or the like, into subcutaneous tissue or other types of tissue, such as the epidermis, dermis, and different types of sub-dermal tissue such as muscle. The embodiments of the present fluid delivery devices shown in the figures are adapted for use with humans; however, those of ordinary skill in the art will, in light of this disclosure, understand that other embodiments may be adapted for use with animals.

The present fluid delivery devices may be characterized as ports, fluid delivery ports, injection ports, injection aides, infusion ports or infusion devices. The present fluid delivery systems may be characterized as injection systems or infusion systems. The portion of the present fluid delivery devices initially contacted by an insertion or injection structure (such as a needle) resides outside a user's body, and may be characterized as an outside-the-skin body, or an outside-the-skin portion.

Figure 2:
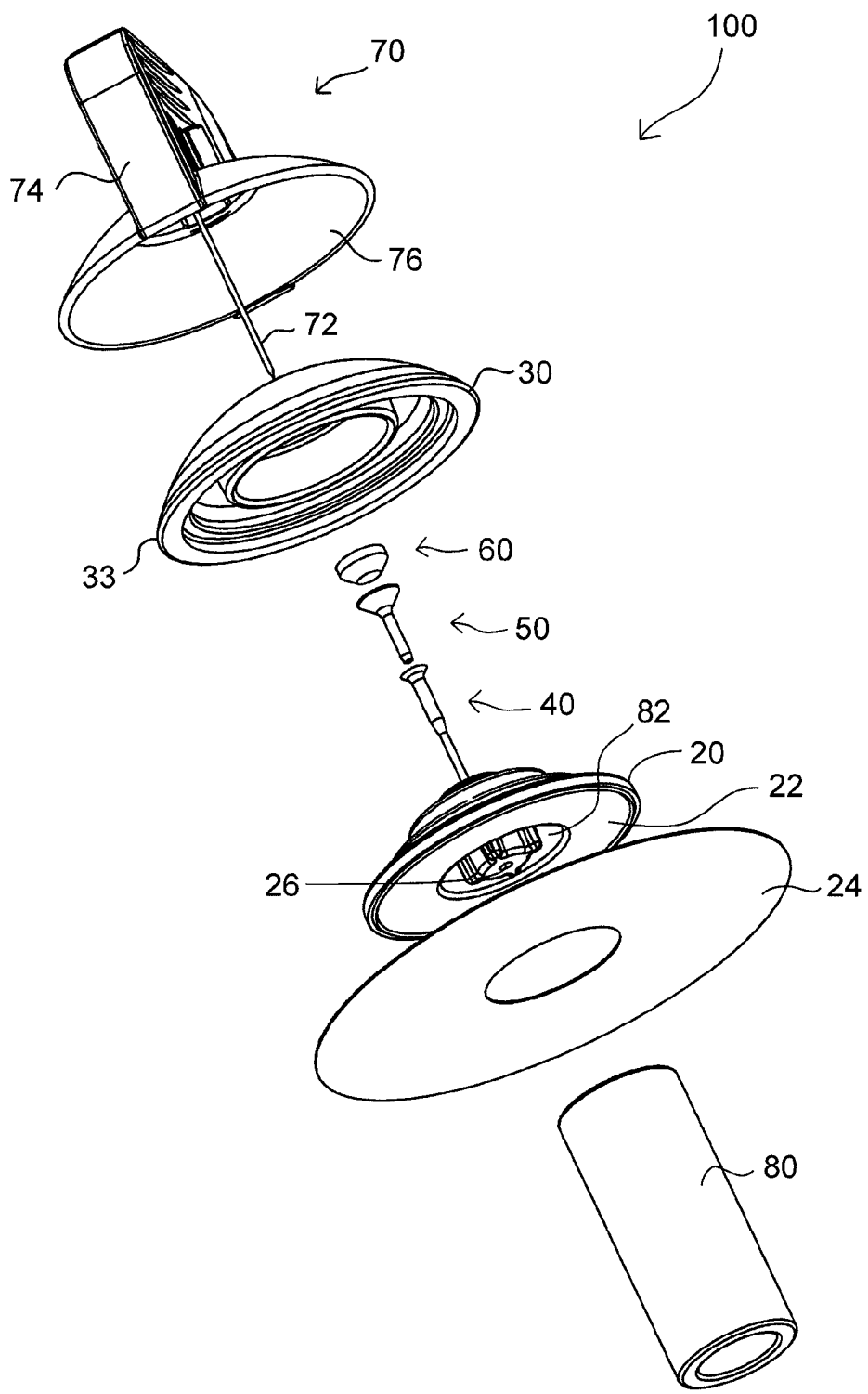
FIG. 2 is another perspective exploded view of the embodiment shown in FIG. 1.

FIGS. 1 and 2 show perspective, exploded views of one embodiment of the present fluid delivery devices. Fluid delivery device 100 includes a two-piece body (unnumbered) that includes a base 20 (which also may be characterized as bottom piece 20) and a cap 30 (which also may be characterized as top piece 30). In other embodiments, the body may be primarily one-piece and include a septum retention member. In still other embodiments, the body may comprise three or more pieces, or as few as one piece. Cap 30 may be coupled to base 20 through any suitable attachment means known to those skilled in the art, such as ultrasonic welding, an adhesive, or the like. Alternatively, cap 30 may be configured to be coupled to the base through a friction-fit type engagement that may be fortified through any suitable attachment means known to those skilled in the art.

In the embodiment shown in FIGS. 1 and 2, cap 30 has a curved outer surface, which also may be characterized as convex. Cap 30 includes a top 32 and an outer perimeter 33 characterized by its outermost edge, and which also may be characterized as an outer perimeter of the body. In this embodiment, outer perimeter 33 also defines the outermost portion of the body. Base 20 includes a bottom surface 22. Broadly, fluid delivery device 100 is an example of a fluid delivery device configured for installation to a user. More specifically, fluid delivery device 100 is an example of a fluid delivery device configured to adhere to a living being's skin. In this embodiment, the configuration is achieved with the generically-depicted adhesive layer 24 (which may include a protective backing sheet). Such adhesive layers are well known in the art, and may include a pad having two opposing, adhesive-coated sides, one of which is attached to the relevant portion of bottom surface 22 and the other of which will be attached to a user's body once a backing sheet has been removed. Alternatively, one of the two opposing sides may be welded (e.g., ultrasonically welded) to bottom surface 22 instead of being attached via an adhesive. As yet another alternative of achieving such a configuration, a portion (e.g., all) of bottom surface 22 may be configured to adhere to a living being's skin, such as by making the bottom surface material from a material that chemically reacts with and adheres to skin.

The bodies of the embodiments of the present fluid delivery devices shown in the figures are examples of bodies that lack a snap-fit compatible upper exterior portion, which means that the upper portion of outer surface of the body is configured not to work with another component designed for snap-fit engagement. By contrast, the body of the fluid delivery device in U.S. Pat. No. 6,685,674 includes a snap-fit compatible upper exterior portion, which is cover 18. The bodies of the embodiments of the present fluid delivery devices shown in the figures also are examples of bodies that lack a substantially-rectangular skin-contacting wing extending at an acute angle from an adjacent upstream body portion. By contrast, the body of the fluid delivery device in U.S. Pat. No. 6,685,674 includes a substantially-rectangular skin-contacting wing (i.e., wing 12) extending at an acute angle from an adjacent upstream body portion (i.e., cover 18).

The body shown in FIGS. 1 and 2 includes a body passageway that extends from opening 34 in cap 30 through the passageway in base 20. The base passageway extends from base entrance opening 25 to base exit opening 26. The body passageway is centered within the body of this embodiment; however, in other embodiments, some or all of the body passageway may be off-center, such as an upper portion of the body passageway that is accessible at an angle to the user's skin other than substantially perpendicular. Because the body passageway in this embodiment is centered in the body, insertion and injection needles may enter the body at a substantially perpendicular angle to the bottom surface of the device (which is bottom surface 22 in this embodiment).

Fluid delivery device 100 also includes a cannula 40, a needle guide 50 and a septum 60. A portion of cannula 40 (specifically, an upper portion) resides, or is positioned, within the body passageway, and a portion (specifically, a lower portion) extends from bottom surface 22 when the fluid delivery device is assembled and ready for normal use. A portion (and, in some embodiments, all) of needle guide 50 resides, or is positioned, within the cannula 40 when the fluid delivery device is assembled, and is positioned to prevent an injection structure (such as a needle) from contacting cannula 40 during injection of fluid, such as insulin. The needle guide also prevents an insertion device (such as an insertion needle) from contacting an upper portion of cannula 40 during installation of the fluid delivery device to a living being. The "installation" of one of the present fluid delivery devices to a living being or a user refers to the process by which a portion of the cannula is inserted below the outer surface of the skin.

For some embodiments of the present fluid delivery devices that include a needle guide (e.g., needle guide 50) and that are configured such that a portion of the body is in direct contact with the needle guide, the portion of the body that makes the direct contact near the top of the needle guide may be configured to have an interference fit with the needle guide, such that the diameter of the top of the needle guide is greater than or equal to the diameter of the portion of the body that it will contact.

A portion (and, in some embodiments, all) of septum 60 resides, or is positioned, within needle guide 50 (or within the cannula in embodiments where a rigid cannula is used) when the fluid delivery device is assembled. As one can see from the arrangement of the elements of fluid delivery device 100, cannula 40 will be positioned upon assembly such that any portion of the cannula that is outside, or above, a living being's skin when the fluid delivery device is used will be positioned within outer perimeter 33 of the body (see also FIG. 12).

Fluid delivery device 100 also includes an insertion device 70 comprising an insertion needle 72 connected to an insertion needle hub 74. An insertion needle cover 76 extends from (e.g., through attachment or integral connection to) insertion needle hub 74, and is configured to cover a portion of cap 30. The body of fluid delivery device 100 and insertion device 70 may be configured in any suitable manner to prevent the rotation of insertion needle 72 within the body, thus reducing any stress on cannula 40 that would otherwise occur if insertion needle 72 rotated within it. One such manner involves configuring needle cover 76 and/or needle hub 72 with one or more protrusions and configuring the exposed surface of cap 30 with one or more corresponding recesses in which the protrusions may reside. Rotation of the needle hub about an axis running through the body passageway may be restricted or inhibited when the protrusion or protrusions are positioned in their corresponding recess or recesses. As another example configuration, the protrusion(s) and recess(es) could be reversed, such that cap 30 possesses the protrusion(s) and the inner surface of cover 76 and/or hub 72 possesses the recess (es).

Fluid delivery device 100 also includes a needle guard 80 designed to prevent a user's inadvertent contact with insertion needle 72 during the user's handling of the fluid delivery device. Base 20 includes a needle guard holding recess 82 that is configured to engage an upper portion of needle guard 80 and hold needle guard 80 through a friction fit, or any other suitable means of engagement. Similarly, insertion device 70 is configured such that needle guard 80 may be secured to insertion device 70 through a friction fit. As a result, after a user has installed fluid delivery device 100 to his or her body and removed the insertion device from the body of the fluid delivery device, the exposed insertion needle 72 can be protected using needle guard 80 prior to disposal of the insertion device.

In other embodiments of the present fluid delivery devices, no needle guard is used. For example, in some such embodiments, the insertion device, or tool, that is used does not include a needle that is continuously exposed. In other such embodiments, the packaging for the fluid delivery device includes a portion that functions as a needle guard.

Figure 3:
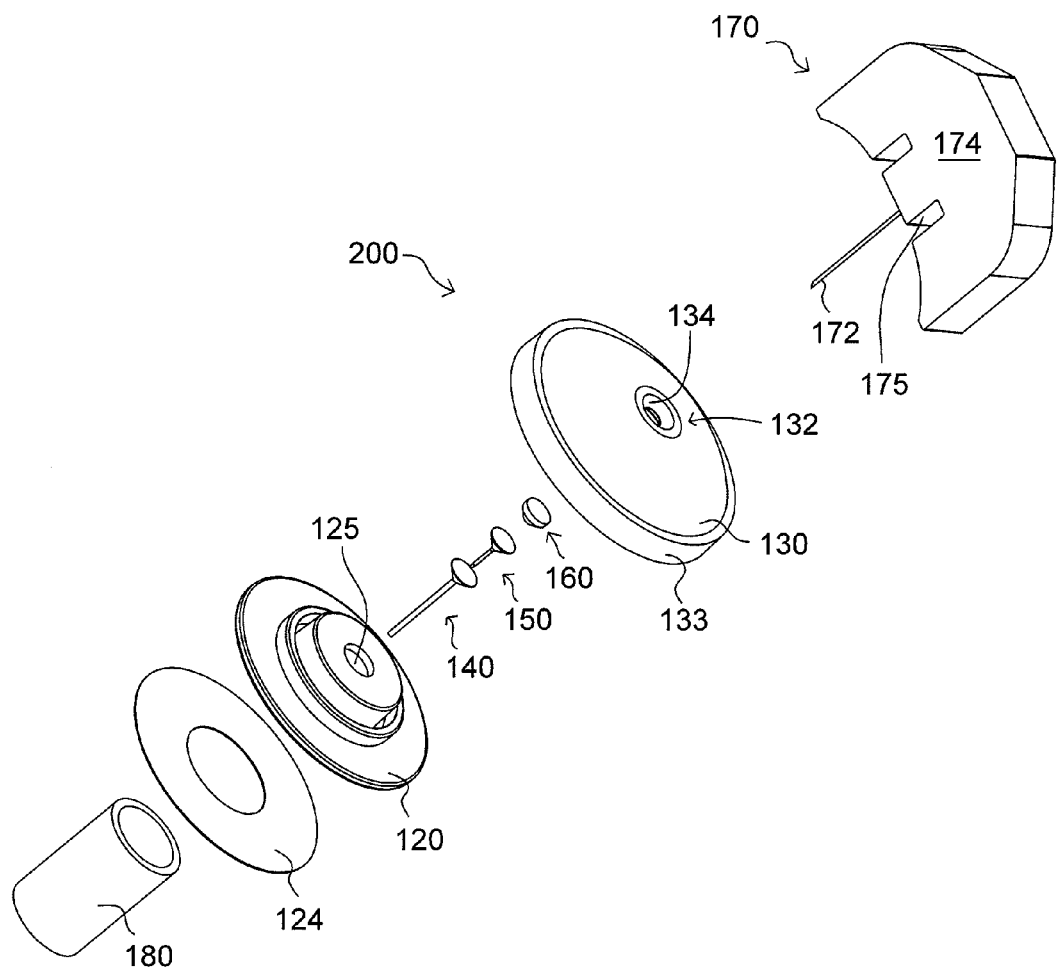
FIG. 3 is a perspective exploded view of another embodiment of the present fluid delivery devices.
Figure 4:
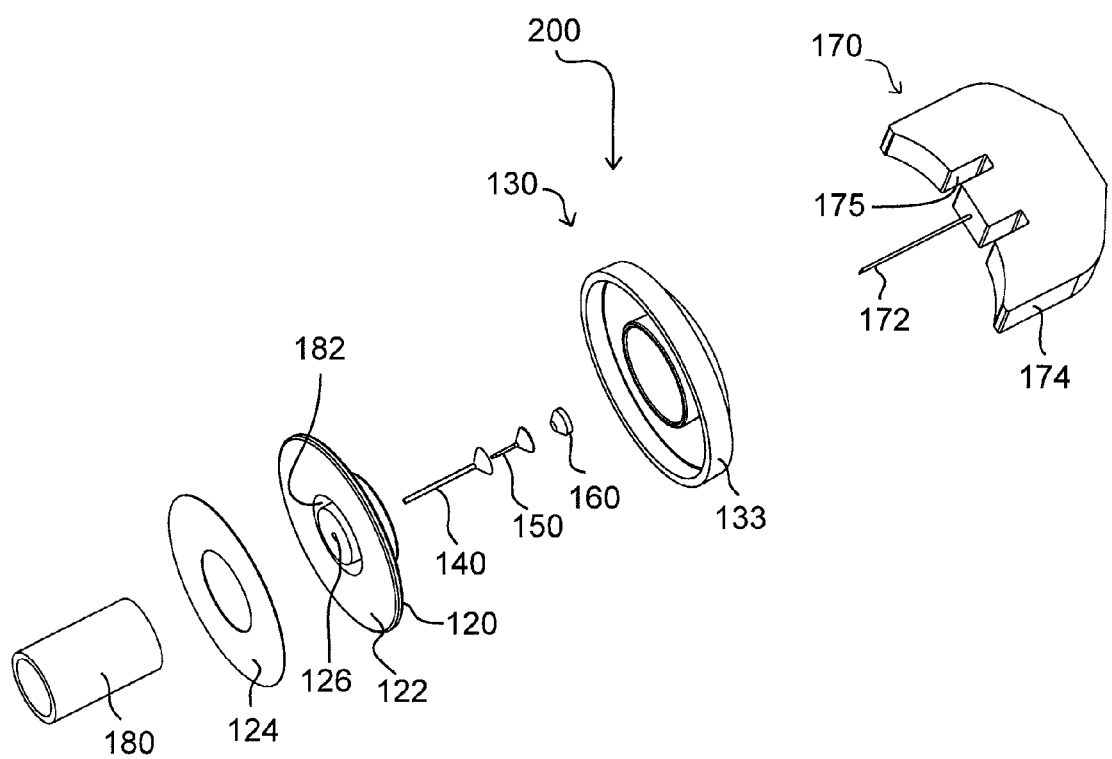
FIG. 4 is another perspective exploded view of the embodiment shown in FIG. 3.

FIGS. 3 and 4 show perspective, exploded views of another embodiment of the present fluid delivery devices. The elements of fluid delivery device 200 are similar in function and shape to the elements of fluid delivery device 100. Consequently, each element is numbered in similar fashion, except by a value of 100 more. Fluid delivery device 200 includes a two-piece body (unnumbered) that includes a base 120 and a cap 130, which is configured to be coupled to the base through any suitable means known to those skilled in the art, such as ultrasonic welding, an adhesive, heat, or like; or through a friction-fitting engagement that could be fortified through any suitable means known to those skilled in the art. In this embodiment, the upper portion of the outer surface of cap 130 is curved, which upper portion also may be characterized as convex. Cap 130 includes a top 132 and an outer perimeter 133 characterized by its outermost edge, and which also may be characterized as an outer perimeter of the body. In this embodiment, outer perimeter 133 also defines the outermost portion of the body. Base 120 includes a bottom surface 122. Fluid delivery device 200, in this embodiment, may be characterized as being configured to adhere to a living being's skin. Specifically, in this embodiment, the configuration is achieved with the generically-depicted adhesive layer 124 (which may include a protective backing sheet) that may be characterized in the same way as adhesive layer 24 described above. Alternatively, another way to achieve the configuration is for a portion of bottom surface 122 to be configured to adhere to a living being's skin, such as by making the bottom surface material from a material that chemically reacts with and adheres to skin.

The body shown in FIGS. 3 and 4 includes a body passage that extends from opening 134 in cap 130 through the passageway in base 120. The base passageway extends from base entrance opening 125 to base exit opening 126. The body passageway is centered within the body of this embodiment; however, in other embodiments, some or all of the body passageway may be off-center, such as an upper portion of the body passageway that is accessible at an angle to user's skin other than substantially perpendicular. Because the body passageway in this embodiment is centered in the body, insertion and injection needles enter the body at a substantially perpendicular angle to the bottom surface of the device (which is bottom surface 122 in this embodiment).

Fluid delivery device 200 also includes a cannula 140, a needle guide 150 and a septum 160. A portion of cannula 140 (specifically, an upper portion) resides, or is positioned, within the body passageway, and a portion (specifically, a lower portion) extends from bottom surface 122 when the fluid delivery device is assembled and ready for normal use. A portion (and, in some embodiments, all) of needle guide 150 resides, or is positioned, within the cannula 140 when the fluid delivery device is assembled, and is positioned to prevent an injection or insertion structure (such as insertion needle 172) from contacting an upper portion of cannula 140 during installation of fluid delivery device 200 to a user or during injection of fluid. A portion (and, in some embodiments, all) of septum 160 resides, or is positioned, within needle guide 150 (or within the cannula in embodiments where a rigid cannula is used) when the fluid delivery device is assembled. As one can see from the arrangement of the elements of fluid delivery device 200, cannula 140 will be positioned upon assembly such that any portion of the cannula that is outside a living being's skin when the fluid delivery device is used will be positioned within outer perimeter 133 of the body.

Fluid delivery device 200 also includes an insertion device 170 comprising an insertion needle 172 connected to an insertion needle hub 174. Fluid delivery device 200 also includes a needle guard 180 designed to prevent a user's inadvertent contact with insertion needle 172 during the user's handling of the fluid delivery device. Base 120 includes a needle guard holding recess 182 that is configured to engage an upper portion of needle guard 180 and hold needle guard 180 through a friction fit, or any other suitable means of engagement. Similarly, insertion needle hub 174 is configured with a recess 175 such that needle guard 180 may be secured to insertion needle hub 174 (and, therefore, insertion device 170) through a friction fit between the guard and the recess. As a result, after a user has installed fluid delivery device 200 to his or her body and removed the insertion device from the fluid delivery device, the exposed insertion needle 172 can be protected using needle guard 180 prior to disposal of the insertion device.

Figure 5:
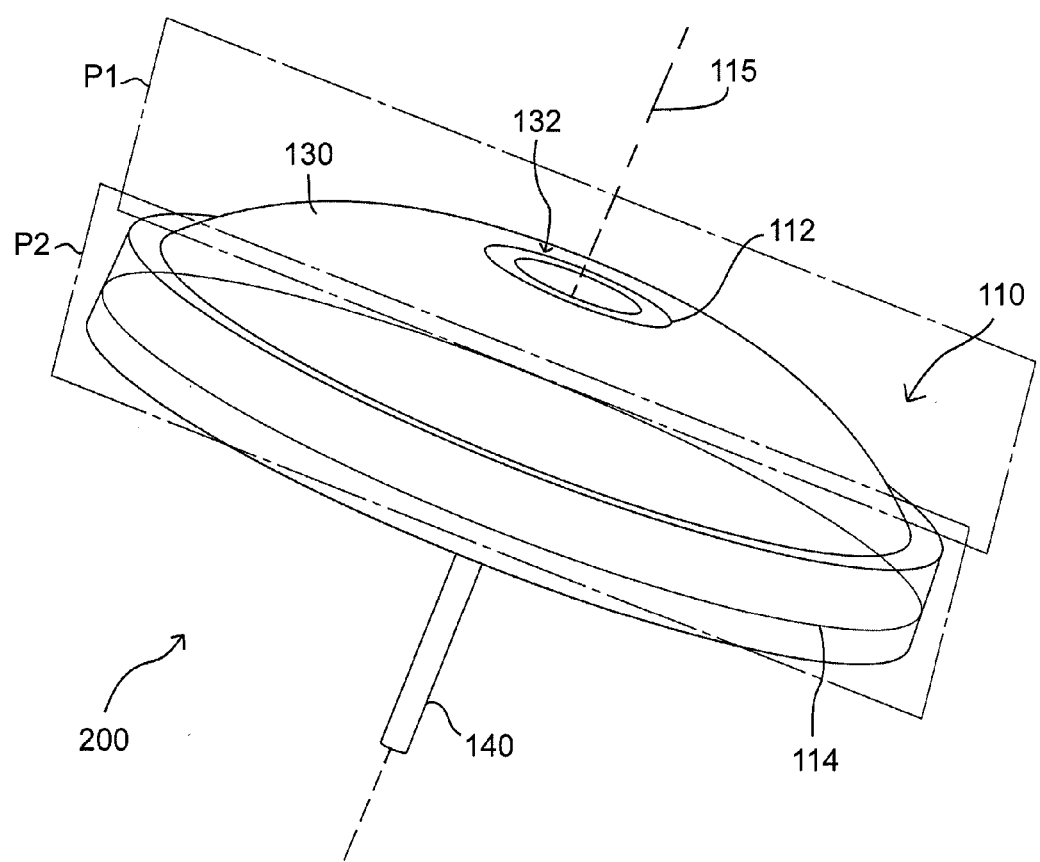
FIG. 5 is a perspective view showing the position of different perimeters of one of the present fluid delivery devices, the different perimeters being positioned in different planes intersecting the device.

FIG. 5 is an incomplete representation of fluid delivery device 200 (the body passageway is not completely depicted) showing that the body 110 (which includes base 120 and cap 130) has a first perimeter 112 at top 132 and a second perimeter 114 that is close to the bottom surface of the body (which is the bottom surface of the base). First perimeter 112 is positioned in a first plane P1, which is perpendicular to axis 115 that is centered within the body passageway (and that is, therefore, parallel to a portion of the body passageway). Second perimeter 114 is positioned in a second plane P2, which is parallel to and downstream of first plane P1. FIG. 6 shows the relationship between axis 115, first perimeter P1 and second perimeter P2. As FIG. 5 shows, second perimeter 114 is greater than first perimeter 112. This means that the linear distance represented by second perimeter 114 (which, for fluid delivery device 200, is equal to the circumference of second perimeter 114) is larger than the linear distance represented by first perimeter 112 (which also is a circumference).

Figure 7A:
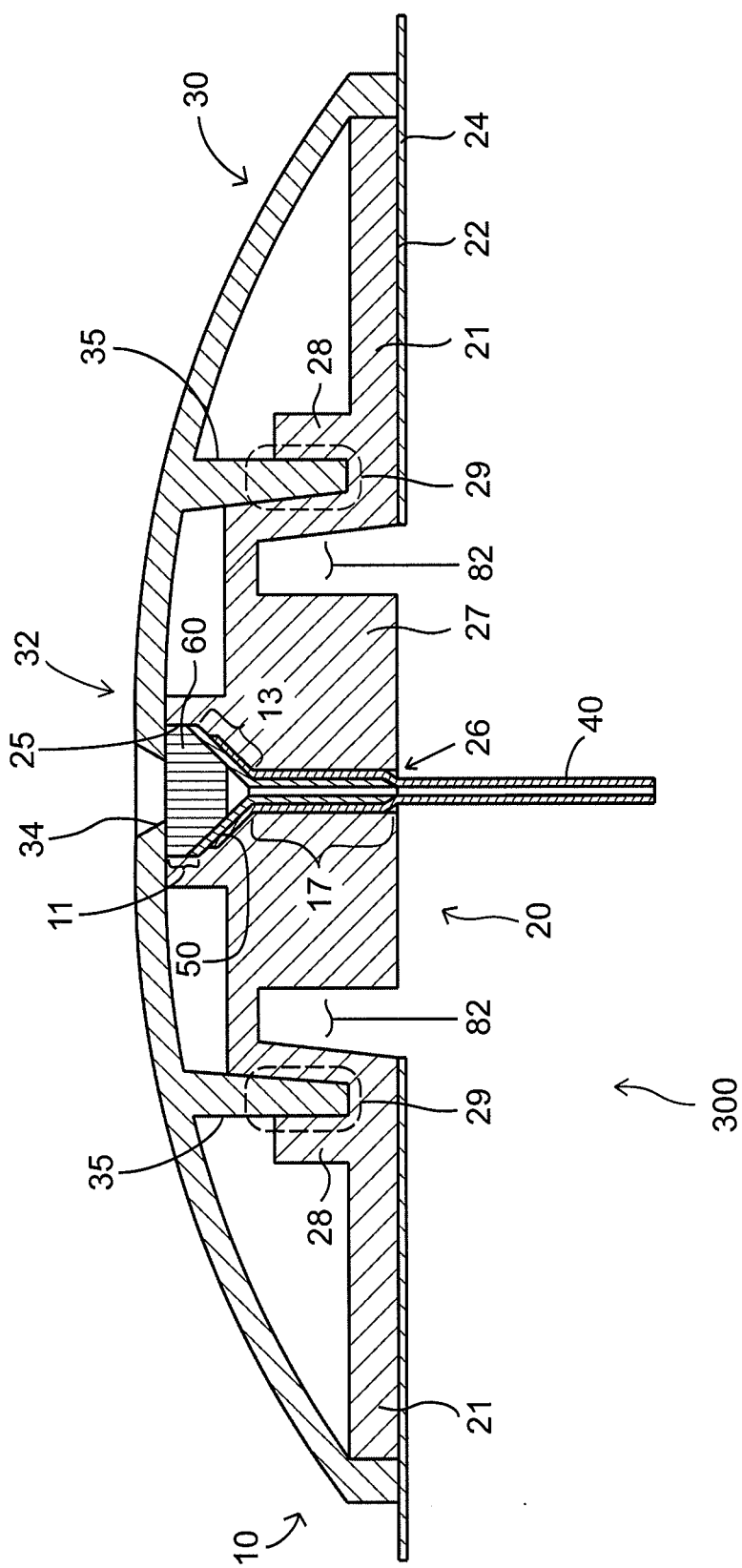
FIG. 7A is a cross-sectional view of one embodiment of the present fluid delivery devices.

FIG. 7A is a cross sectional view of an embodiment of the present fluid delivery devices similar to the embodiment shown in FIGS. 1 and 2. The cross section of fluid delivery device 300 is taken through the center of the device. The numbers used to designate the elements of fluid delivery device 300 are the same as those used to designate the elements of fluid delivery device 100 because of the similarity of the shape and function of the elements. In this figure, the body of fluid delivery device 300 is designated as element 10. A portion of the outer surface of cap 30 is curved and, in this embodiment, substantially convex. The portion of the outer surface of cap 30 nearest the top 32 is flat. The outermost, or widest, portion of the outer surface of cap 30 is cylindrical in shape, and substantially perpendicular to the flat, top portion of the outer surface of cap 30. A substantially cylindrical portion 35 extends downwardly from the inner surface of cap 30, and is configured to engage (or at least contact) a mating recess 29 in base 20 that is defined by an outer substantially cylindrical portion 28 that extends upwardly from flat base portion 21 and an outer side wall of central portion 27 of base 20. The engagement between portion 35 and recess 29 may be configured to be retained by friction between the contacting surfaces shown in FIG. 7A, and may be fortified through any suitable means known to those skilled in the art, such as an adhesive, ultrasonic welding, heat, or the like. Alternatively, no friction-fit configuration may be used, and portion 35 and recess 29 may coupled with any suitable means known to those skilled in the art, such as through ultrasonic welding.

The body passageway of body 10 begins at the opening 34 in cap 30, which extends from the outer surface of cap 30 to the inner surface of cap 30. The term "outer surface" of cap 30 is the surface that is exposed to the user of the fluid delivery device. The term "inner surface" of the cap is the surface that is shielded from exposure to the user of the fluid delivery device. Opening 34 may be tapered, and in this embodiment the taper may be an "inward" taper that is constant, which means the wall defining opening 34 is not curved between the outer and inner surfaces (except for the rounded edges that normally result from traditional manufacturing techniques). Moving downwardly from opening 34, the body passageway includes the base passageway, which extends from base entrance opening 25 to base exit opening 26. The base passageway includes an uppermost portion 11 that is substantially cylindrical, or straight-walled; a lowermost portion 17 that also is substantially cylindrical, or straight-walled; and an intervening portion 13 that is generally tapered. Portion 13 includes an upper segment that is tapered to match the taper of an upper portion of needle guide 50, a lower segment that is tapered to match that taper of an upper portion of cannula 40, and a short non-tapered segment between the upper and lower segments. Exit opening 26 of base 20 may be configured to fit snugly, or closely, against cannula 40, although not shown as such in FIG. 7A.

The outer edge of adhesive layer 24 extends beyond the outer edge of body 10 in FIG. 7A. In other embodiments, the outer edge of adhesive layer 24 may be flush with the outer edge of body 10 (FIG. 8A). In still other embodiments, the outer edge of adhesive layer 24 may be recessed from (or not extend as far as) the outer edge of body 10 (FIG. 8B).

FIG. 7A shows that cannula 40 has a portion extending substantially perpendicularly from bottom surface 22 of base 20, which also may be characterized as the bottom surface of body 10. More specifically, this same portion of cannula 40 (the lower portion) will extend substantially perpendicularly from the bottom surface of the body when fluid delivery device 300 is installed to a living being, such as a human.

FIG. 7A shows that the most narrow portion of opening 34, which is the portion of the opening that resides in the inner surface of cap 30, is smaller in diameter than the diameter of the top surface of septum 60. As a result, the septum may be characterized as "capped" by cap 30. This configuration of cap 30 and septum 60 helps to keep septum 60 in place when an insertion or injection structure (such as a needle) is withdrawn from septum 60.

Furthermore, the widest portion of opening 34 in this embodiment, which is the portion of the opening that resides in the outer surface of cap 30, is smaller in diameter than the diameter of the top surface of septum 60. This configuration of cap 30 and septum 60 also helps to keep septum 60 in place during removal of an insertion/injection structure, such as a needle, from septum 60. The portion of cap 30 that overlaps a portion of the top of septum 60 may be characterized as a septum retaining shoulder. The septum retaining shoulder of other embodiments of the present fluid delivery devices may include more of the cap than just the portion that overlaps a portion of the top of the septum.

FIG. 7A also shows that septum 60 has a septum top surface that has a septum top surface portion that is accessible to an injection needle during normal use of the fluid delivery device ("normal use" does not include accessing the septum with an injection needle by somehow inserting the injection needle through the portion of cap 30 that overlaps a portion of the septum's top surface). That septum top surface portion has a perimeter (which, in this embodiment, is circular in shape because opening 34 is circular) that is smaller than the outer perimeter of the top surface of the septum.

Fluid delivery device 300 shown in FIG. 7A is an example of fluid delivery device that includes a septum having a bottom surface, the bottommost location of which is closer to the top of the body than to the bottom of the body. Characterized another way, the bottommost portion of the septum is closer to the topmost portion of the body than to the bottommost portion of the body.

Figure 7B:
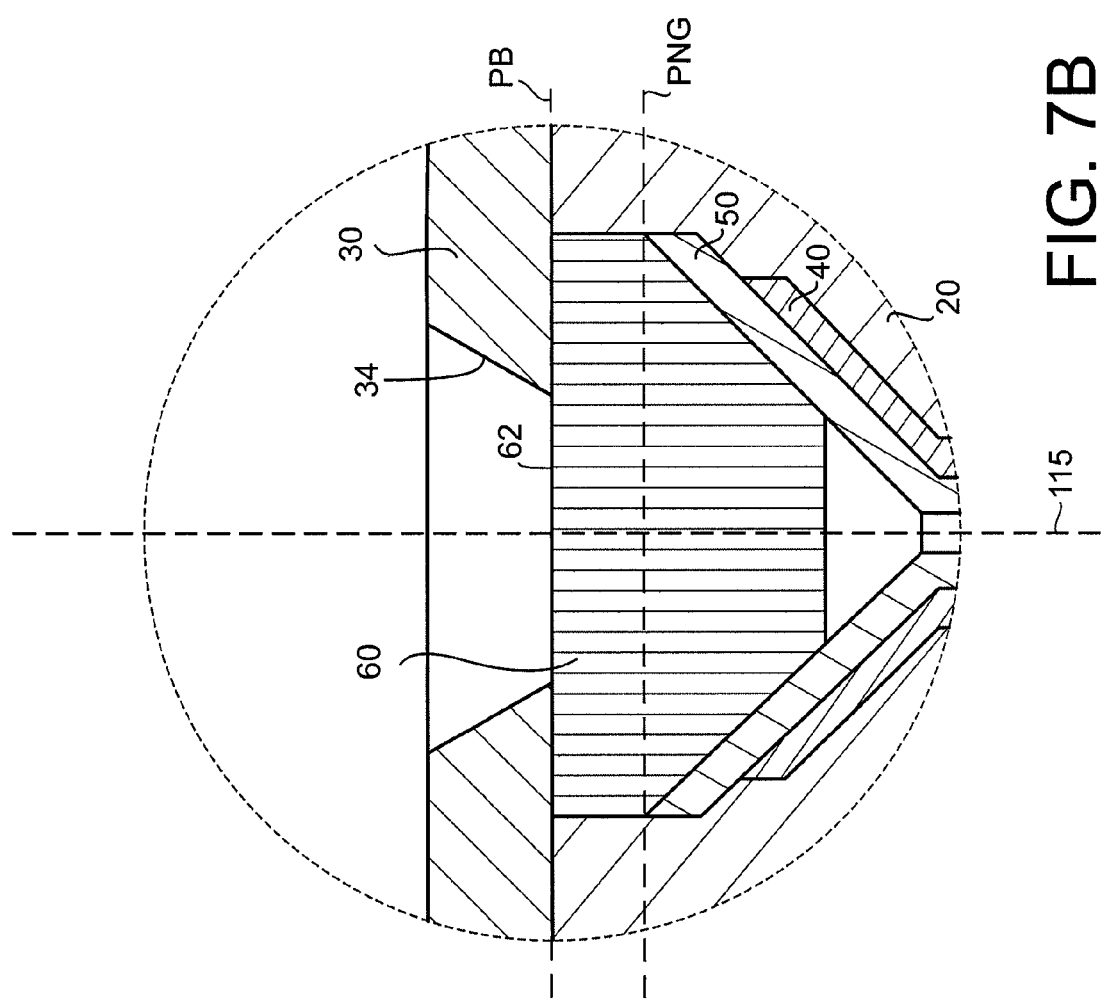
FIG. 7B is an enlarged detail of one aspect of the embodiment shown in FIG. 7A.

FIG. 7B shows an enlarged detail view of the portion of fluid delivery device 300 surrounding septum 60. Septum 60 includes a portion positioned within the body passageway. In this embodiment, the portion comprises all of septum 60. Septum 60 also may be characterized as being positioned "within" the base passageway. This means that the top surface 62 of septum 60 is at or below a plane PB in which the top of base 20 resides; plane PB is substantially perpendicular to axis 115, which is substantially centered within the body passageway (and that is, therefore, substantially parallel to a portion of the body passageway). The portion of septum 60 that is positioned "within" needle guide 50 is the portion of septum 60 that is at or below a plane PNG in which the top of needle guide 50 resides, and which is parallel to and downstream of plane PB.

FIGS. 9A and 9B are detail views showing different configurations of cannulas and needle guides. FIG. 9A shows that needle guide 50 includes a portion 52 that is tapered inwardly (also characterizable as an upper tapered portion). Tapered portion 52 also may be characterized as a funnel-shaped portion. Tapered portion 52 has a length LT (length LT may be an arc length for curved tapered portions like the one in FIG. 9C). The embodiment of tapered portion 52 shown in FIGS. 9A and 9B also may be characterized as an upper section of needle guide 50 that has a taper of constant angle. In contrast, needle guide 16 of infusion hub assembly 10 of U.S. Pat. No. 6,685,674 lacks an upper section having a taper of constant angle; the taper of the upper section of needle guide 16 has a variable angle, and therefore gives the upper section of the needle guide wall bordering the needle guide passageway a curved shape rather than the straight shape of tapered portion 52 of the fluid delivery device shown partially in FIGS. 9A and 9B. Tapered portion 52 may meet the lower straight portion (also characterizable as the shaft, or stem) of needle guide 50 at a substantially hard change of angle, as shown in FIGS. 9A and 9B. However, in other embodiments of the present fluid delivery devices, the two portions meet over a section that is tapered in a curved manner, such as section 59 shown in FIG. 9C. Needle guide 50 has a needle guide passageway 53 that includes an upper tapered portion (defined by portion 52 in the FIGS. 9A and 9B embodiments, and by portions 52 and 59 in the FIG. 9C embodiment) and a lower straight portion (see FIG. 7A), which also may be characterized as a cylindrical portion, or section.

The embodiment of the fluid delivery device shown (partially) in FIGS. 9A and 9B is an example of one that includes a septum in direct contact with the upper tapered portion of a needle guide for at least half or more of the length of the upper tapered portion.

Cannula 40 includes a portion 42 that is tapered inwardly (also characterizable as an upper tapered portion). As FIG. 9A shows, tapered portion 42 is in contact with tapered portion 52. Tapered portion 42 may have a taper of constant angle, as shown in FIGS. 9A and 9B, or may have a taper of varying angle (also characterizable as a curved taper), as shown in FIG. 9C (although not shown, it may also have a combination of both, like portions 52 and 59 of needle guide 50). Cannula 40 also includes a cannula passageway 41 that includes an upper tapered portion (defined by portion 42), a lower straight portion (see FIG. 7A), and an intermediate straight portion that is separated from the lower straight portion by a short tapered portion configured to be in close contact with the bottom of needle guide 50 (see FIG. 7A). The embodiment of cannula 40 in FIG. 9B has a top outer edge that terminates along the same longitudinal plane (parallel to an axis positioned in and running through the body passageway) as the top outer edge of needle guide 50. This is not true of the embodiment of cannula 40 in FIG. 9A, which has a top outer edge that terminates closer to the center of the body passageway than the top outer edge of the needle guide 50.

The accessible portion 63 of the top surface 62 of septum 60 of the embodiment of the present fluid delivery devices depicted in FIG. 9A has a perimeter and a greatest width that are both greater than the largest perimeter and the largest width of cannula 40. FIGS. 9B and 9C show embodiments of the present fluid delivery device where this relationship is not true. FIGS. 9A, 9B, and 9C each show that top surface 62 of septum 60 is recessed below the top 32 of cap 30. Top surface 62 also may be characterized as residing in a plane (not shown) that is downstream of plane P1 shown in FIGS. 5 and 6, and that is parallel to planes P1 and P2.

As one can see in FIGS. 9A-9C, septum 60 has, in this embodiment, a side wall that includes a cylindrical portion 65 and a portion 67 that is tapered inwardly (or in a downstream direction), and a bottom surface 68 that meets portion 67. The side wall of septum 60 (from cylindrical portion 65 to tapered portion 67) is in close contact with a surrounding portion of the fluid delivery device, which in these embodiments comprises a portion of base 20 and a portion of tapered portion 52 of needle guide 50. The configuration of the fluid delivery device shown in these figures also may be characterized as including a septum that has a lower half that is in close contact with a surrounding portion of the fluid delivery device (which, in this embodiment, comprises a portion (specifically, tapered portion 52) of needle guide 50), and as including a septum that has a middle that is in close contact with a surrounding portion of the fluid delivery device (which, in this embodiment, again comprises a portion (specifically, tapered portion 52) of needle guide 50). Septum 60, like all the septa depicted in the present figures, is an example of a septum lacking a cylindrical hollow section extending upwardly from the center of the bottom surface of the septum. By contrast, the septum 20 of the fluid delivery device in U.S. Pat. No. 6,685,674 includes a cylindrical hollow section extending upwardly from the center of its bottom surface. Septum 60, like all the septa depicted in the present figures, is an example of a septum that is configured such that any portion of it that is occupied by an insertion needle during fluid delivery device installation is substantially re-occupied by septum material after the insertion needle is removed. By contrast, the septum 20 of the fluid delivery device in U.S. Pat. No. 6,685,674 includes a cylindrical hollow section extending upwardly from the center of its bottom surface that will not be substantially re-occupied by septum material after introducing needle 30 is removed.

A portion of each embodiment of septum 60 shown in FIGS. 9A-9C (specifically, the lower portion defined by tapered portion 67) is positioned within the needle guide passageway 53, and, more specifically, within the upper tapered portion of needle guide passageway 53. There is an open space 69 beneath, or downstream of, bottom surface 68. Open space 69 is within the body passageway generally, within the base passageway more specifically, within a portion of cannula 40 even more specifically, and most specifically within (and downstream of) tapered portion 52 of the embodiment of needle guide 50 shown in FIGS. 9A and 9B, and within (and downstream of) curved tapered portion 59 of the embodiment of needle guide 50 shown in FIG. 9C.

Figure 10A:
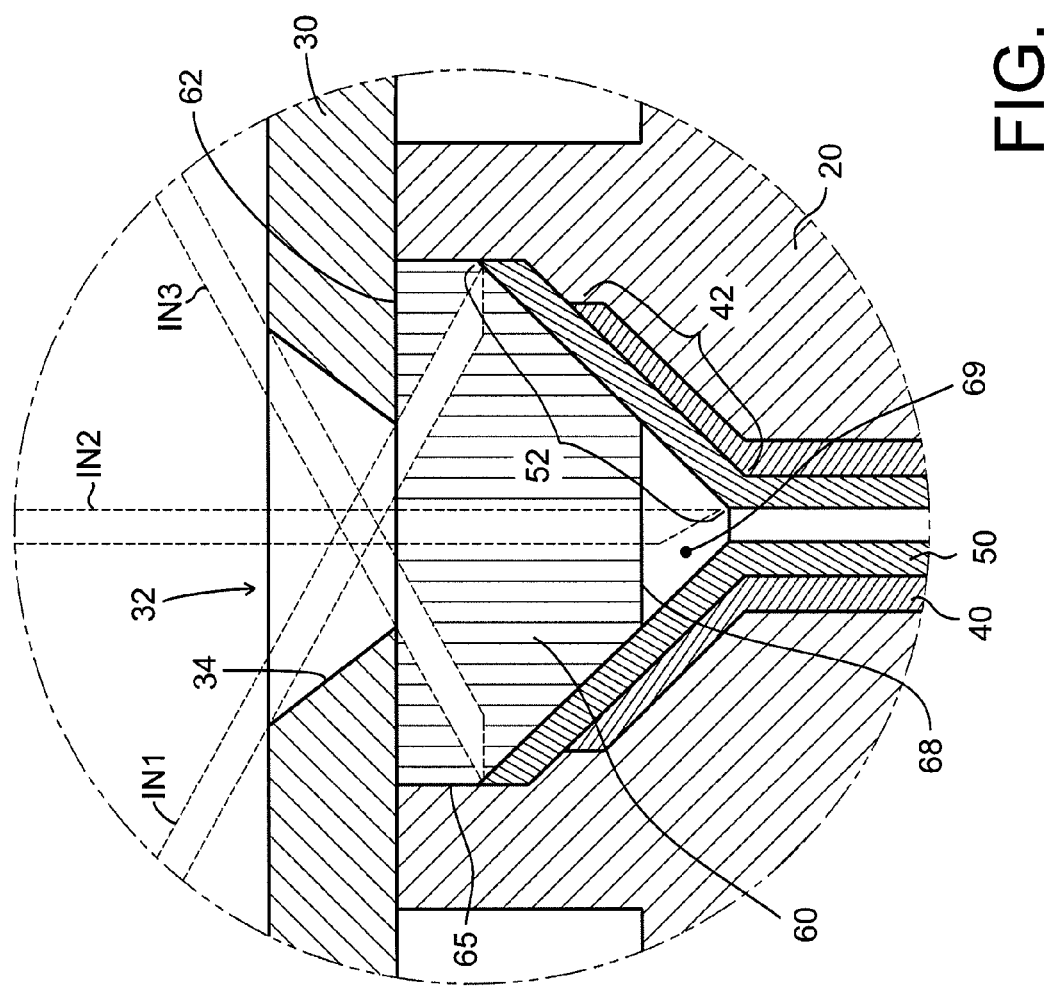
FIG. 10A is an enlarged detail view showing a different configuration of the portion of the fluid delivery device shown in FIG. 7A that includes, and is located around, the septum.

FIG. 10A is another detail view of an embodiment of one of the present septa and the surrounding portion of the fluid delivery device. This figure shows that in some embodiments, the present fluid delivery devices can be configured such that an injection needle (three of which are shown in phantom as IN1, IN2 and IN3) that has passed through the septum (e.g., septum 60) to deliver medication to a living being during use of the fluid delivery device either (a) exits the septum into an open space (e.g., open space 69) that is within the body passageway and downstream of at least a portion of the septum bottom surface (e.g., bottom surface 68), or (b) contacts a portion of the fluid delivery device (e.g., needle guide 50 and, more specifically, upper tapered portion 52) that is tapered inwardly. Injection needles IN1 and IN3 satisfy (b), and injection needle IN2 satisfies (a). This (b) part of this configuration of the fluid delivery device is achieved, in this embodiment, by configuring opening 34, septum 60, the body (and, in particular, base 20), and needle guide 50 such that no matter how shallow the angle of entry of a suitably-sized injection needle (such as, in some embodiments of the present fluid delivery devices, one that is 28 to 31 gauge), that injection needle (e.g., injection needle IN1 or IN3) will exit the septum into an inwardly-tapered portion of the fluid delivery device (which takes the form of tapered portion 52 of needle guide 50 in this embodiment). FIG. 10A also shows an example of a septum (septum 60) that is configured such that an injection needle that penetrates the septum (to delivery medication to a patient, for example) and exits the septum into open space (open space 69) cannot re-penetrate the septum. By contrast, it appears that septum 20 of the fluid delivery device in U.S. Pat. No. 6,685,674 is configured such that an injection needle that penetrates the septum and exits the septum into open space can re-penetrate the septum. Furthermore, fluid delivery device 100 is an example of a fluid delivery device that is configured such that an injection needle that penetrates the septum and exits the septum into open space cannot re-penetrate the septum. By contrast, the fluid delivery device in U.S. Pat. No. 6,685,674 appears to be configured such that an injection needle that penetrates septum 20 and exits septum 20 into open space can re-penetrate septum 20.

Some of the embodiments of the septum of the present fluid delivery devices shown in the figures (e.g., the septum shown in FIGS. 1-4) have a circular profile from their tops to their bottoms (although not necessarily a consistent circular profile, like they would have if they were cylindrically-shaped). Other embodiments may have a rectangular (e.g., square) profile, or a profile having any shape suited to a desired application. A septum of one of the present fluid delivery device may be solid or pre-slit (as is known in the art). The slit may extend from the top to the bottom, or may start at the top and extend partway toward the bottom, or may start at the bottom and extend partway toward the top. Solid septa also may be characterized as non-slit or non-split septa.

Figure 10B:
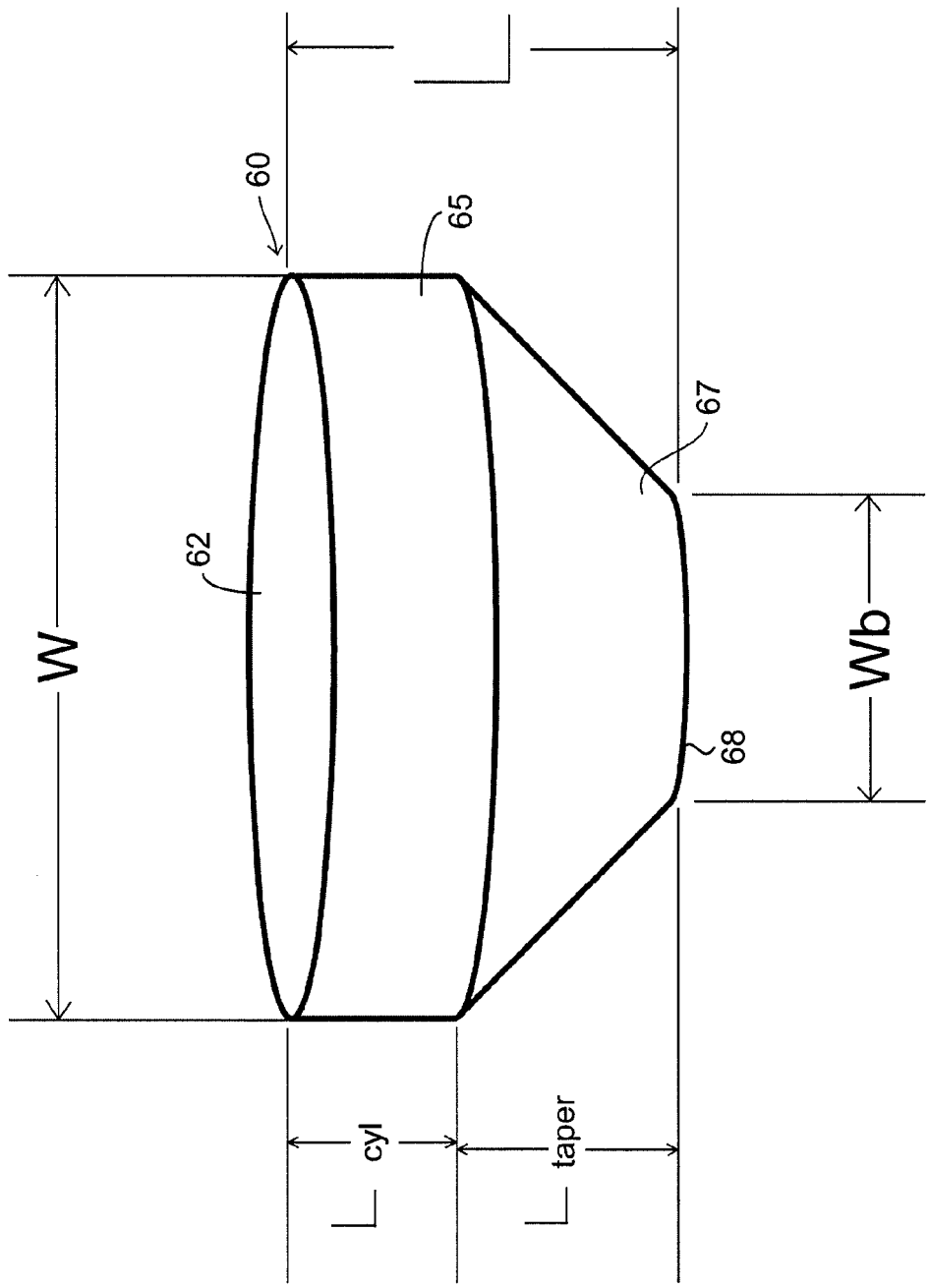
FIG. 10B is an enlarged perspective view of one of the septa that may be used with some embodiments of the present fluid delivery devices.

An embodiment of one of the present septa is shown in FIG. 10B. The embodiment of septum 60 shown in this figure has a length, or thickness, L that extends from top surface 62 to bottom surface 68. In the FIG. 10B embodiment, L is the greatest length of the septum (or the greatest thickness of the septum). The cylindrical portion of the septum 65 has a length, or thickness, $L_{cyl}$. The bottom tapered portion 67 of the depicted embodiment of septum 60 has a length, or thickness, $L_{taper}$. The depicted embodiment of septum 60 also has a width W, which, in this embodiment, is the width of the top of the septum and the width of the widest portion of the septum (or the greatest width of the septum). Width $W_b$ is the width of the bottom of the bottom of the depicted embodiment of septum 60. In this and other embodiments of septum 60, W is greater than L. Characterized another way, the greatest width of the embodiment of septum 60 shown in FIG. 10B is greater than (meaning it has a larger value than) the greatest length of the septum. The ratio between the two may range from greater than one to greater than 10, including any integer in between, such as 2, 3, 4, 5, 6, 7, 8, and 9, and including any non-integer between the integers, such as 5.1, 5.2, and 5.3. In other embodiments, W is more than 10 times greater than L. In this and other embodiments of septum 60, $L_{cyl}$ is less than $L_{taper}$. In some embodiments, $L_{taper}$ may be up to ten times greater than $L_{cyl}$, including all integers and non-integers in that range. In other embodiments, $L_{taper}$ is greater than 10 times $L_{cyl}$. In still other embodiments, $L_{cyl}$ is up to ten times greater than $L_{taper}$, including all integers and non-integers in that range; in other embodiments, $L_{cyl}$ is more than ten times greater than $L_{taper}$, in between those values. The term "length" with respect to the length of a septum is the distance running in the direction of the normal flow of fluid through the fluid delivery device; thus, the "length" of a septum is the distance from the topmost portion of the septum to the bottommost portion of the septum.

Returning to FIG. 10A, this figure also illustrates that bottom surface of septum 68 is configured and septum 60 is positioned such that if an injection needle (e.g., injection needle IN2) that has passed through septum 60 to deliver medication to a living being during use of the fluid delivery device exits the septum bottom surface 68 into open space 69, that open space is within the body passageway and downstream of at least a portion of the septum bottom surface 68. In the context of the present fluid delivery devices and methods, the term "open space" does not include the tiny gaps between the septum and the needle guide that exist because of the minute differences in the shape of their mating surfaces. There is no open space between the cylindrical portion of the embodiment of septum 60 and the surrounding portion of the embodiment of base 20 shown in FIG. 10A (see FIG. 18A for an embodiment where this is not true). As a result, the embodiment of the fluid delivery device in FIG. 10A may be characterized as one that is configured such that, if an injection needle exits the septum in open space, the open space is part of the fluid channel of the body. "Fluid channel" is defined as the portion of the body passageway through which fluid is designed to flow in order to reach a user to which the fluid delivery device is installed. The terms "downstream" and "below" are defined relative to the normal flow through the fluid delivery device of fluid traveling to a user through the cannula of the device. Thus, for fluid delivery device 300 for example, septum 60 is downstream of (and below) opening 34 in cap 30, needle guide 50 is downstream of (and below) the septum, the straight or cylindrical portion of the needle guide is downstream of (and below) the tapered portion of the needle guide, etc.

Figure 11A:
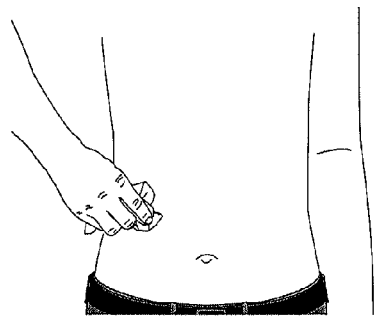
FIGS. 11A-11L show different stages in one method of inserting and injecting through one embodiment of the present fluid delivery devices.
Figure 11B:
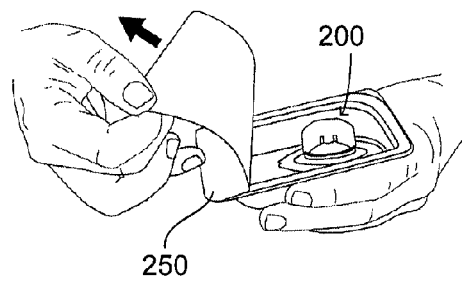
Figure 11C:
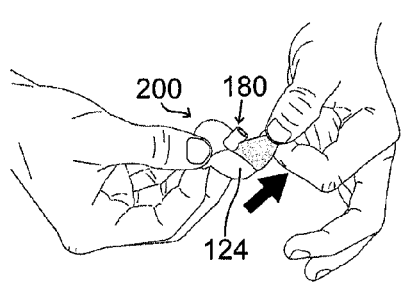
Figure 11D:
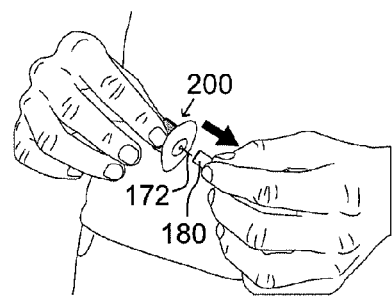
Figure 11E:
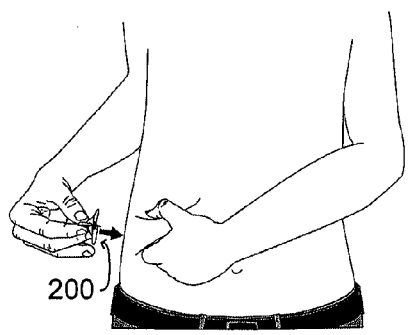
Figure 11F:
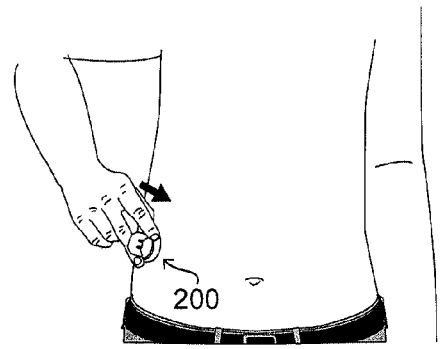
Figure 11G:
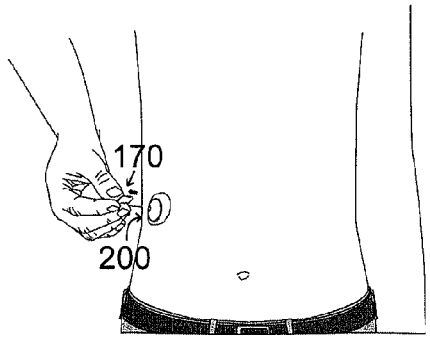
Figure 11H:
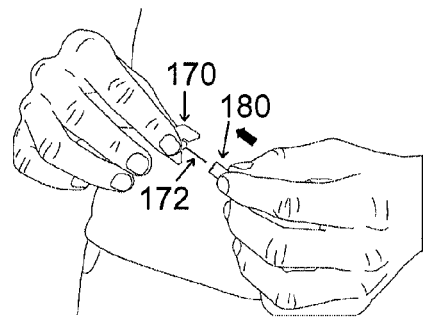
Figure 11I:
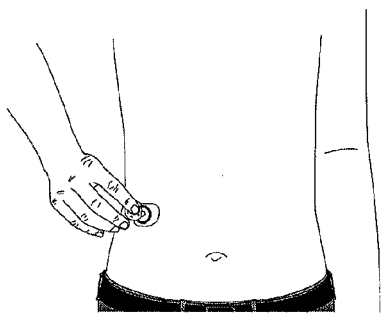
Figure 11J:
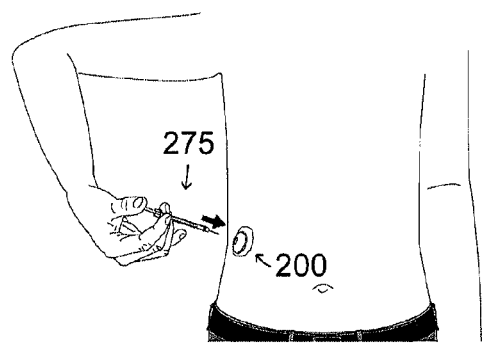
Figure 11K:
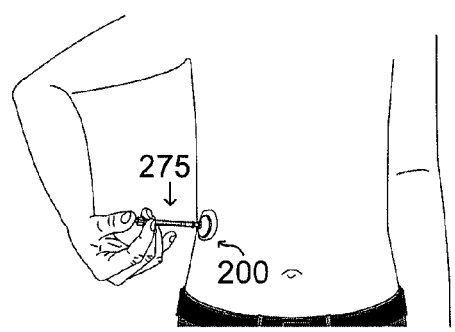
Figure 11L:
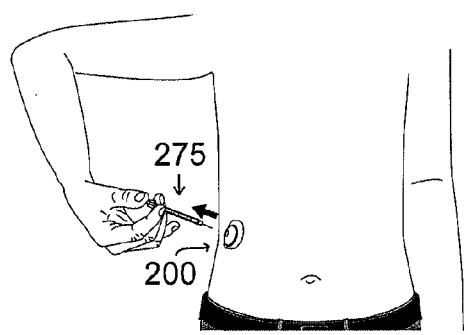

FIGS. 11A-11L are partial views showing the different stages of one method of normal use of one of the present fluid delivery devices to deliver fluid, such as insulin, to the body of a user. FIG. 11A shows a user swabbing with alcohol or a similar disinfectant a portion of the skin to which fluid delivery device 200 will be installed. FIG. 11B shows that the present fluid delivery devices may be sold sterilized in packages. Specifically, FIG. 11B shows a user opening package 250 containing a sterilized fluid delivery device 200. FIG. 11C shows the user removing the protective backing from adhesive 124. FIG. 11D shows the user removing needle guard 180 from the remainder of fluid delivery device 200 without touching the sterile insertion needle 172 with his fingers. FIG. 11E shows the user pinching his skin at the desired site of installation and installing the fluid delivery device 200 to his body with adequate speed and force to ensure that the relevant portions of the insertion needle and cannula are completely inserted in his body tissue. FIG. 11F shows the user pressing the adhesive layer of fluid delivery device 200 firmly against his skin. FIG. 11G shows the user removing the insertion device 170 (and, thus, insertion needle 172). FIG. 11H shows the user covering insertion needle 172 with needle guard 180 prior to disposing insertion device 170. FIG. 11I shows the user ensuring that the septum of fluid delivery device 200 is clean before using it. FIG. 11J shows the user using an injection device 275 (in this embodiment, a standard syringe) to locate and puncture the septum of fluid delivery device 200. FIG. 11K shows the user injecting the fluid directly into the body passageway of fluid delivery device 200. FIG. 11L shows the user removing and disposing of the injection device 275 after injecting the fluid.

Figure 12:
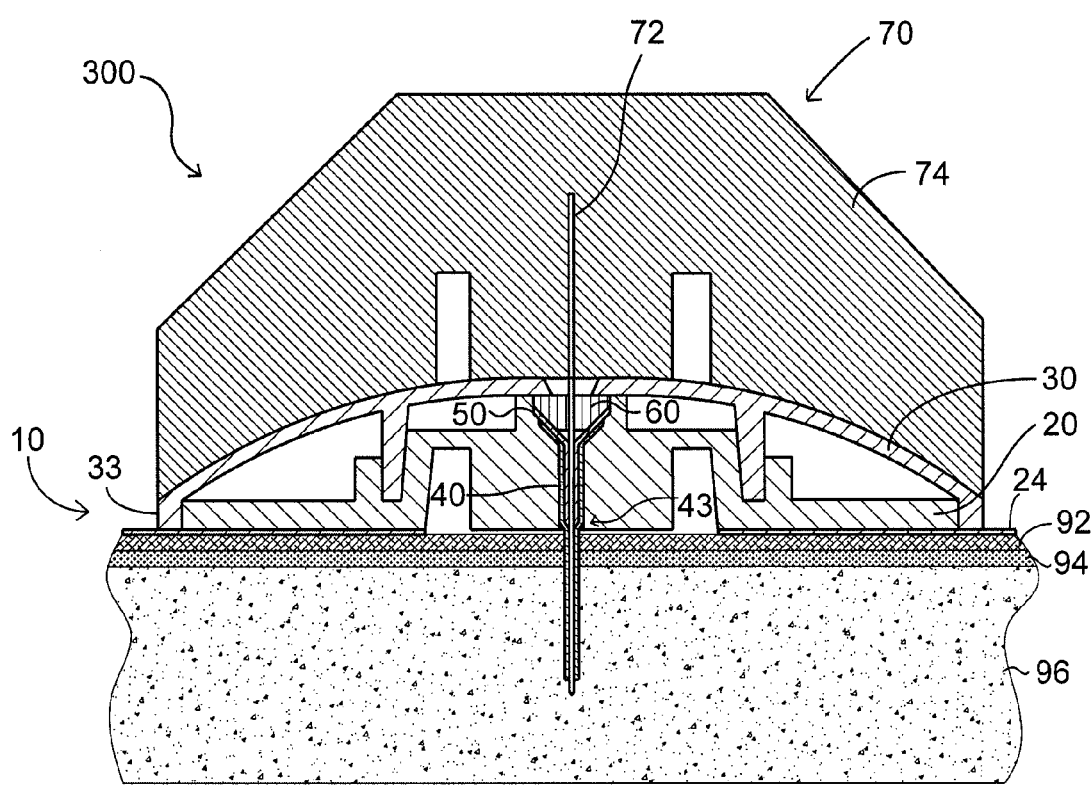
FIG. 12 is a cross-sectional view showing one embodiment of the present fluid delivery devices installed to a user.

FIG. 12 is a cross-sectional view showing fluid delivery device 300 installed to a user. FIG. 12 shows that the end of insertion needle 72 extends slightly beyond the end of cannula 40 because the insertion needle is responsible for piercing the user's body tissue, which includes epidermis 92, dermis 94 and subcutaneous tissue 96. This figure (as does FIG. 7A) also shows that cannula 40 may include a necked-down portion 43, also characterizable as a tapered portion, positioned along cannula 40 to taper inwardly at the lowest end of needle guide 50. The portion of cannula downstream of necked-down portion 43 fits snugly around insertion needle 72 for the purpose of reducing the likelihood that it will buckle, crimp or bend as the fluid delivery device is installed to a user. The friction between the lower portion of the cannula passageway and the outer surface of insertion needle 72 is a force that contributes to the reduction in that likelihood. Although not shown, the lowermost end of cannula 40 may terminate coincident with insertion needle 72 and be configured with the same angle of taper as insertion needle 72 to further the reduction in that likelihood. The portion of cannula 40 immediately below necked-down portion 43 is a portion of cannula 40 positioned outside the user's skin when the fluid delivery device is used, and is positioned within outer perimeter 33 of body 10.

As shown in FIG. 12, fluid delivery device 300 is an example of a fluid delivery device that is configured such that a needle (e.g., insertion needle 72, which may have a centerpoint tip (as depicted) or a beveled tip) sized to help insert a portion of the cannula (e.g., cannula 40) into a living being cannot pierce the cannula during normal installation of the fluid delivery device. This configuration is achieved, in this embodiment, through the use a of needle guide having a needle guide passageway having a diameter that is substantially similar to the diameter of insertion needle 72. Insertion needle 72 would not, during normal installation of fluid delivery device 300, be able to contact the lower portion of cannula 40 even if there was no necked-down portion 43 because of the close fit between the inner surface of the needle guide passageway (which also may be characterized as a needle guide passageway wall) and insertion needle 72.

Figure 13:
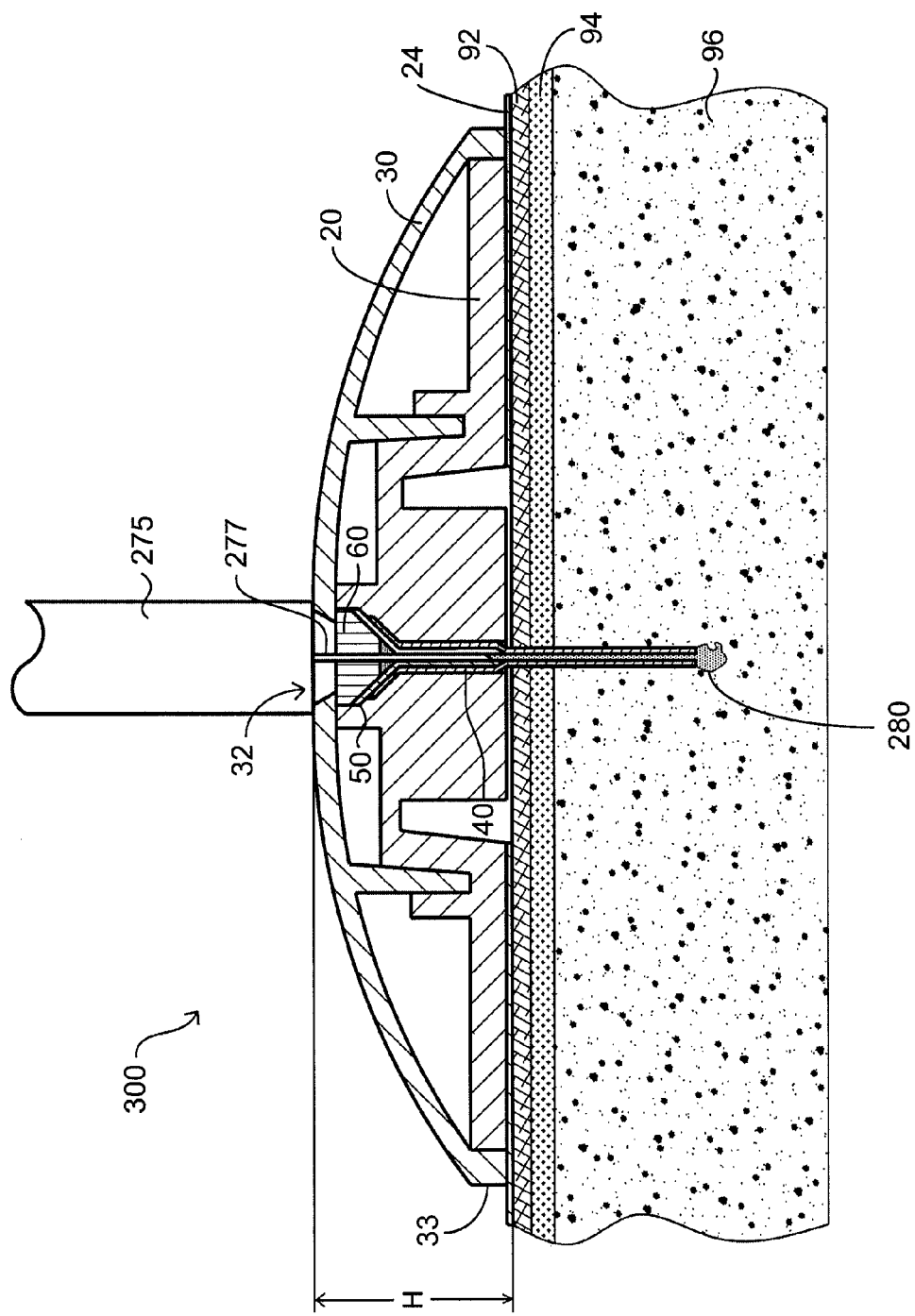
FIG. 13 is a cross-sectional view showing one embodiment of the present fluid delivery devices installed to a user, and further shows the position of an injection device (a syringe and syringe needle in the depicted embodiment) within the installed device.

FIG. 13 is a cross-sectional view showing fluid delivery device 300 installed to a user, and an injection device or structure (an injection needle, in this embodiment) delivering fluid into the subcutaneous tissue of a user. Injection device 275 (which, in this embodiment, is a standard syringe) is shown having its injection structure 277 (which, in this embodiment, is a standard syringe needle) inserted in fluid delivery device 300 and delivering fluid 280 to subcutaneous tissue 96 of a user. This figure shows that fluid delivery device 300 has a height H that extends from top 32 to the bottom of adhesive layer 24, and that height H is chosen to be greater than the length of needle 277 of injection device 275 (such as needle lengths of ⁵⁄₁₆ inches, ⅜ inches or ½ inches). By choosing height H in this way, and by configuring fluid delivery device 300 in such a way that the bottom, or lowermost end, of needle guide 50 is below the end of injection needle 277 when the injection needle is in the position shown, one ensures that the injection needle will not reach an exposed portion of the cannula passageway of cannula 40 during fluid delivery, the "exposed portion" of the cannula passageway of cannula 40 being the portion of the cannula passageway in direct contact with fluid 280.

As shown in FIG. 13, fluid delivery device 300 is an example of a fluid delivery device that includes a cannula having a cannula passageway wall portion (a "wall" of a passageway is the surface that defines the passageway) that will be exposed to fluid during fluid delivery and that has a perimeter (which, in this embodiment, comprises a diameter) that has a substantially identical size to the perimeter (which, in this embodiment, comprises a diameter) of the stem portion of the needle guide of the fluid delivery device.

Figure 14:
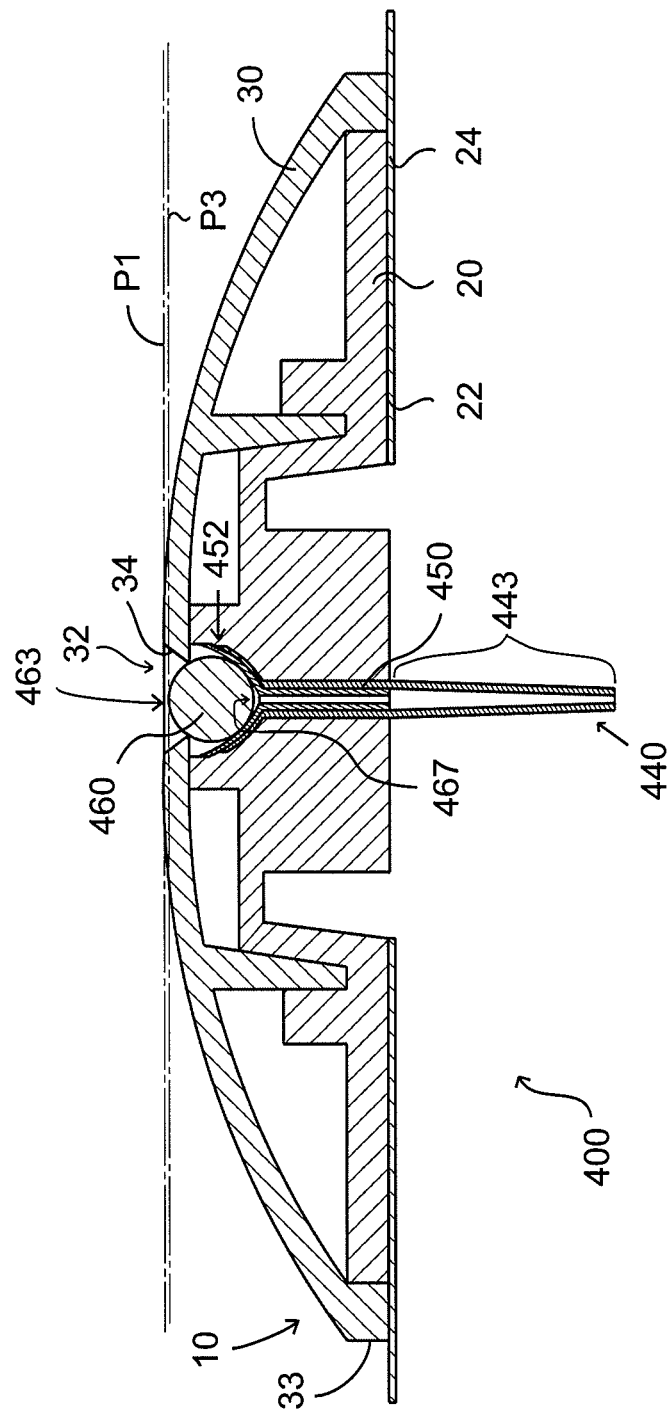

FIGS. 14-17 show different embodiments of the present fluid delivery devices having different configurations of septa from each other and from the previously-illustrated embodiments. The upper portions of the needle guides and cannulas, and therefore the shapes of the body and base passageways, also are different. Fluid delivery device 400 shown in FIG. 14 includes a spherical septum 460, which also may be characterized as a round septum. Opening 34 of cap 30 is tapered in a downstream direction such that its most narrow portion resides in the inner surface of cap 30. As FIG. 14 shows, that most narrow portion is smaller in diameter (shapes other than circular are possible for all embodiments of the openings in the caps of the present fluid delivery devices that have caps) than the diameter of septum 460, such that cap 30 has a septum retaining shoulder that will resist any upward, or upstream, movement of septum 460 when an injection structure such as an injection needle is withdrawn from septum 460. Septum 460 has a top 463 and a bottom 467. Top 463 resides in a plane P3 that is parallel to and downstream of plane P1 in which the top of cap 30 (and, therefore, body 10) resides. Septum 460 also includes a bottom surface and a top surface that meet each other in the middle of septum 460, half-way between top 463 and bottom 467. Both the bottom and top surfaces may be characterized as being curved. Both also may be characterized as being convex. A portion of septum 460 is positioned within the body passageway; more specifically, septum 460 is positioned entirely within the body passageway. A portion of septum 460 is positioned within cannula 440; more specifically a portion of septum 460 is positioned within an upper portion of cannula 440. A portion of septum 460 is positioned within needle guide 450; more specifically, a majority of septum 460 is positioned within needle guide 450; even more specifically, a majority of septum 460 is positioned within the upper tapered portion 452 of needle guide 450, which upper tapered portion has a curved taper, not a taper of constant angle.

FIG. 14 also shows other suitable configurations for a needle guide and cannula combination. Needle guide 450 possesses a non-tapered tip (or bottommost end). Cannula 440 also possesses a lower portion 443 that is located outside the body of the device (and, thus, may be characterized as "exposed") and that is tapered over the entire exposed portion, in contrast to the short necked-down portion 43 shown in FIG. 12. Fluid delivery device 400 is another example of a fluid delivery device that is configured such that a needle sized to help insert a portion of the cannula (e.g., cannula 440) into a living being cannot pierce the cannula during normal installation of the fluid delivery device because the needle guide that is used has a needle guide passageway that has a diameter that is substantially similar to the diameter of a standard insertion needle.

Figure 15:
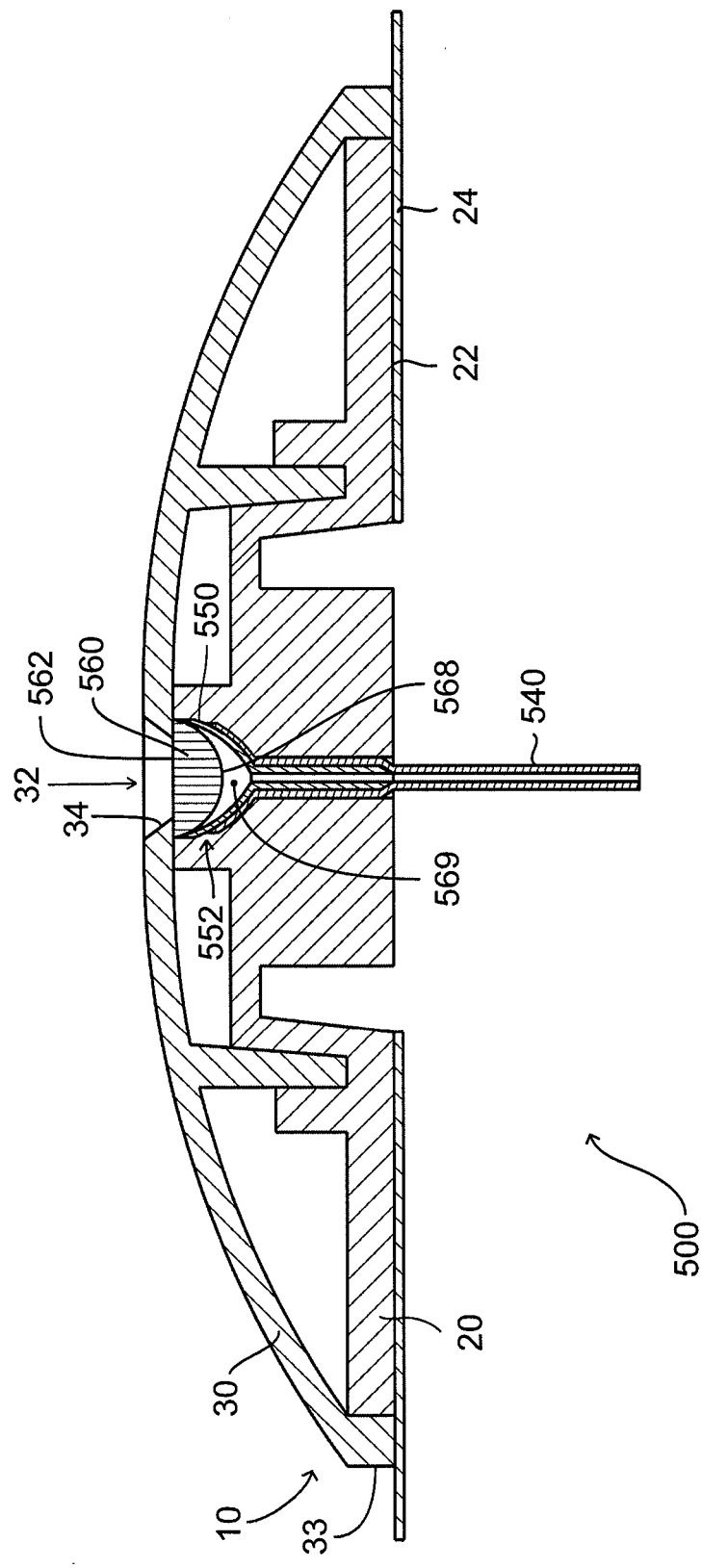

Fluid delivery device 500 shown in FIG. 15 includes a septum 560 having a flat, circular-shaped top surface 562 and a curved, convex-shaped bottom surface 568 that meets top surface 562. A portion of septum 560 is positioned within the body passageway; more specifically, septum 560 is positioned entirely within the body passageway. A portion of septum 560 is positioned within cannula 540; more specifically a portion of septum 560 is positioned within an upper portion of cannula 540. A portion of septum 560 is positioned within needle guide 550; more specifically, septum 560 is positioned entirely within needle guide 550; even more specifically, septum 560 is positioned entirely within the upper tapered portion 552 of needle guide 550, which upper tapered portion has a curved taper, not a taper of constant angle. Fluid delivery device 500 is an example of a fluid delivery device that is configured such that an injection needle (such as injection needle IN1, IN2 or IN3 shown in FIG. 10) that has passed through the septum (e.g., septum 560) to deliver medication to a living being during use of the fluid delivery device either (a) exits the septum into an open space (e.g., open space 569) that is within the body passageway (and, more specifically, within tapered portion 552 of needle guide 550) and downstream of at least a portion of the curved septum bottom surface (e.g., curved bottom surface 568), or (b) contacts a portion of the fluid delivery device (e.g., needle guide 550 and, more specifically, tapered portion 552) that is tapered inwardly (and, more specifically, tapered inwardly in a curved manner).

Figure 16:
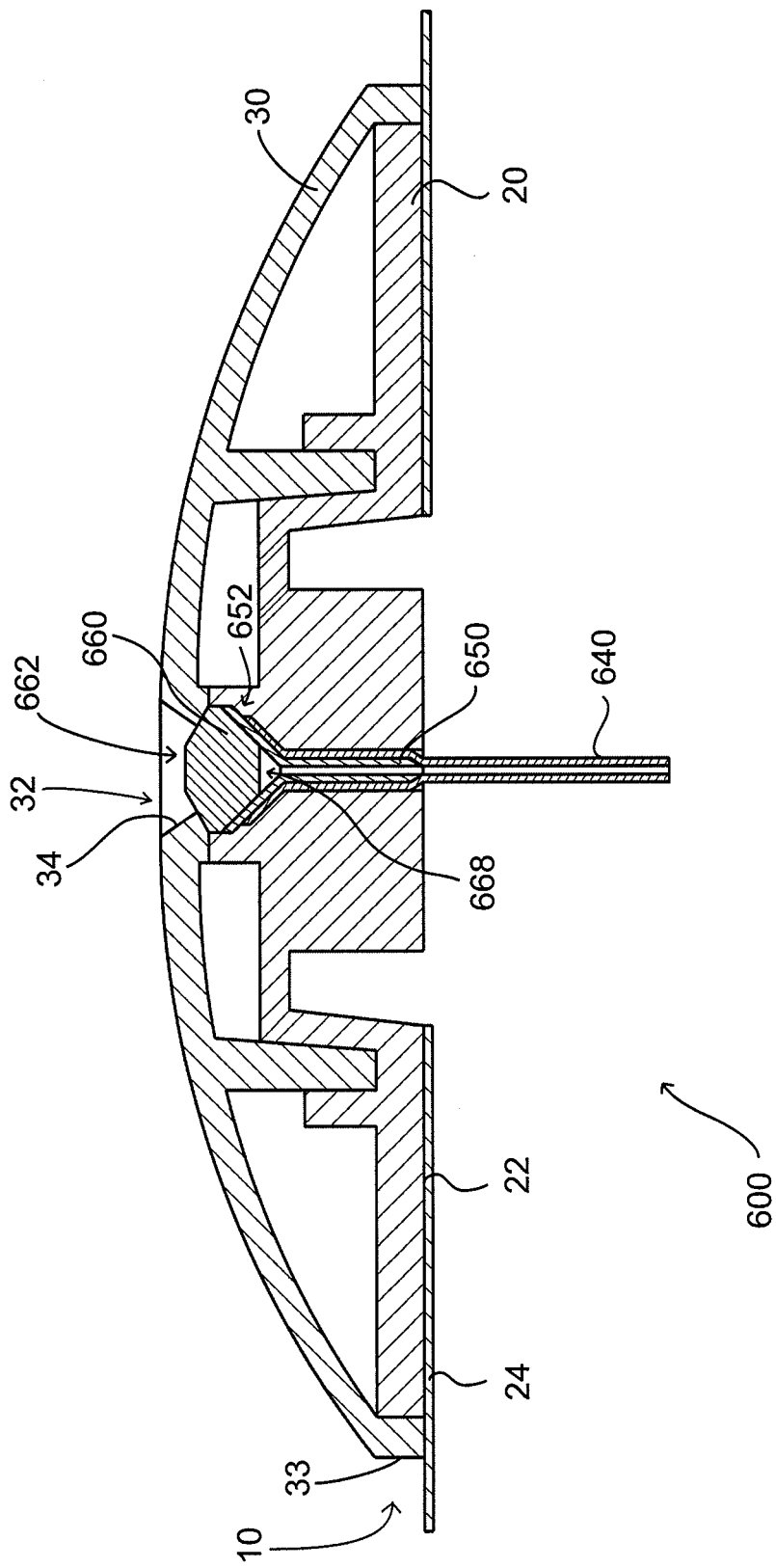

FIG. 16 shows fluid delivery device 600, which includes septum 660 having a top surface 662 that includes a flat top portion positioned in plane that is parallel to plane P1 shown in other figures, and an outwardly tapered portion. The outwardly tapered portion of septum 660 meets a side wall that is perpendicular to the flat top portion of top surface 662 and to flat bottom portion of bottom surface 668. Bottom surface 668 also includes an inwardly tapered portion extending between the flat bottom portion and the side wall of septum 660. The portion of septum 660 defined by the inwardly tapered portion of the bottom surface is positioned within needle guide 650 and, more specifically, within the tapered portion 652 of needle guide 650. A portion of septum 660 is positioned within cannula 640; more specifically a portion of septum 660 is positioned within an upper portion of cannula 640. A portion of septum 650 is positioned within opening 34 of cap 30. The septum retaining shoulder of cap 30 that retains septum 660 is tapered outwardly, as shown. The majority of the profile of septum 660, moving from the flat top portion of top surface 662 to the bottom flat portion of bottom surface 668, is in close contact with a surrounding portion of fluid delivery device 600.

Fluid delivery device 700 shown in FIG. 17 includes septum 760, which has a top surface 762 and a bottom surface 768 that are parallel to each other and to plane P1 shown in other figures. Thus, septum 760 has a length that is unitary across its width. Septum 760 is disc-shaped. FIG. 17 depicts one embodiment of a septum having a portion (and, in this embodiment, the portion comprises all of the septum) having a width that is greater than the portion's length (or, in this embodiment, the portion's thickness); more specifically, this figure depicts one embodiment of a septum having a portion (and, in this embodiment, the portion comprises all of the septum) having a width that is at least twice as great as the portion's length (or, in this embodiment, the portion's thickness); more specifically, this figure depicts one embodiment of a septum having a portion (and, in this embodiment, the portion comprises all of the septum) having a width that is at least three times as great as the portion's length (or, in this embodiment, the portion's thickness); more specifically, this figure depicts one embodiment of a septum having a portion (and, in this embodiment, the portion comprises all of the septum) having a width that is at least four times as great as the portion's length (or, in this embodiment, the portion's thickness); more specifically, this figure depicts one embodiment of a septum having a portion (and, in this embodiment, the portion comprises all of the septum) having a width that is at least five times as great as the portion's length (or, in this embodiment, the portion's thickness); more specifically, this figure depicts one embodiment of a septum having a portion (and, in this embodiment, the portion comprises all of the septum) having a width that is at least six times as great as the portion's length (or, in this embodiment, the portion's thickness); more specifically, this figure depicts one embodiment of a septum having a portion (and, in this embodiment, the portion comprises all of the septum) having a width that is at least seven times as great as the portion's length (or, in this embodiment, the portion's thickness); and even more specifically, this figure depicts one embodiment of a septum having a portion (and, in this embodiment, the portion comprises all of the septum) having a width that is at least eight times as great as the portion's length (or, in this embodiment, the portion's thickness).

Needle guide 750 of fluid delivery device 700 includes both a tapered portion 752 and a cylindrical portion extending upstream, or upwardly, from tapered portion 752. Septum 760 may be characterized as being positioned within the body passageway; more specifically, within the base passageway; more specifically, within the needle guide; and even more specifically, within the upper cylindrical portion of needle guide 750. No portion of septum 760 is positioned within cannula 740. Septum 760 includes an outer side profile that is in close contact with a surrounding portion of the fluid delivery device (which portion, in this embodiment, comprises needle guide 750 and, more specifically, the upper cylindrical portion of needle guide 750).

Fluid delivery device 700 is an example of a fluid delivery device that is configured such that an injection needle (such as injection needle IN1, IN2 or IN3 shown in FIG. 10) that has passed through the septum (e.g., septum 760) to deliver medication to a living being during use of the fluid delivery device either (a) exits the septum into an open space (e.g., open space 769) that is within the body passageway (and, more specifically, within tapered portion 752 of needle guide 750) and downstream of at least a portion of the septum bottom surface (e.g., bottom surface 768), or (b) contacts a cylindrically-shaped, substantially constant-diameter portion of the fluid delivery device (e.g., the upper cylindrical portion of needle guide 750.

Figure 18B:
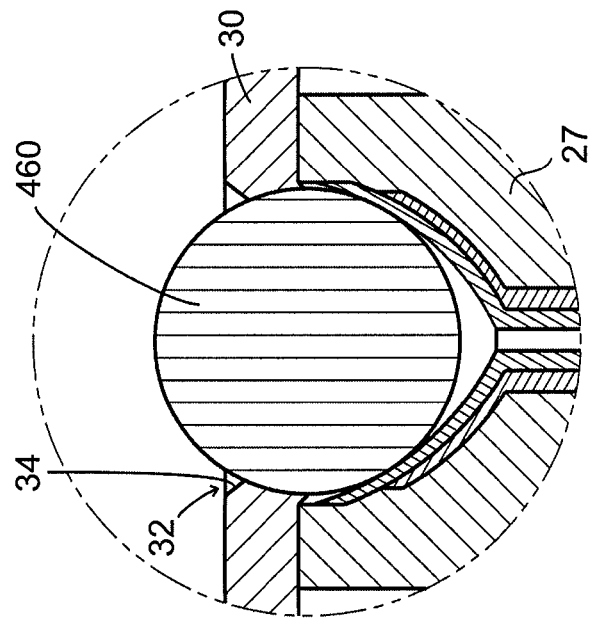
FIGS. 18A and 18B are enlarged detail views showing different configurations of the portion of the fluid delivery device shown in FIG. 14 that includes, and is located around, the septum.
Figure 18A:
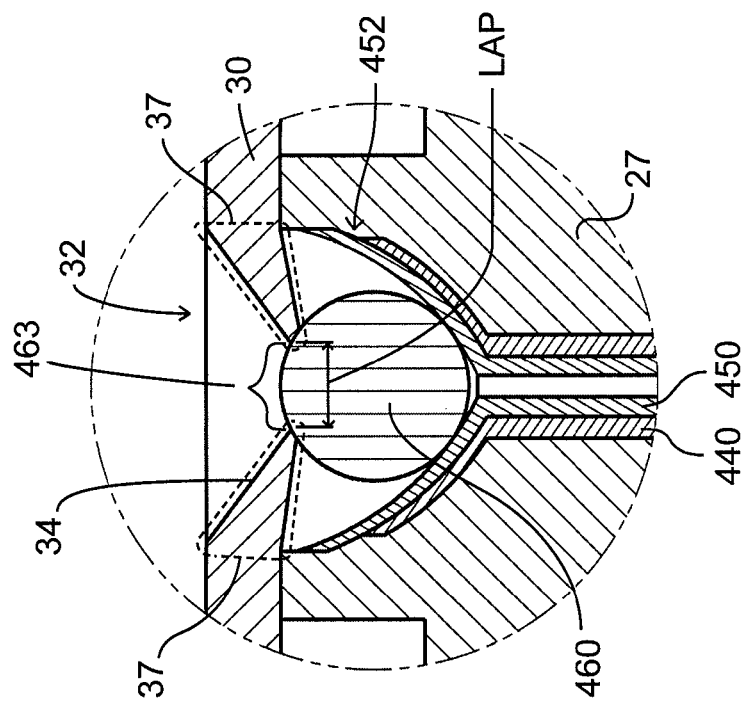

FIGS. 18A and 18B depict different embodiments of septum 460 shown in FIG. 14, and different embodiments of the septum retaining shoulder of cap 30. The version of septum 460 shown in FIG. 18A is spherical but smaller in size than the septum shown in FIG. 14. The septum retaining shoulder of the FIG. 18A embodiment, which is shown in generally dashed lines and designated generally as 37, includes a bottom surface portion that is angled inwardly. The portion of septum retaining shoulder 37 that contacts septum 460 is a curved annular ring that is thicker than the ring contacting the embodiment of septum 460 shown in FIG. 14. The length LAP of accessible portion 463 of the top surface of the version of septum 460 is less than half of the total width of the septum 460. The version of the fluid delivery device shown in FIG. 18A (in combination with FIG. 14) is an example of a fluid delivery device that is configured such that an injection needle (such as injection needle IN1, IN2 or IN3 shown in FIG. 10) that has passed through the septum (e.g., septum 460) to deliver medication to a living being during use of the fluid delivery device either (a) exits the septum into an open space that is within the body passageway (and, more specifically, within tapered portion 452 of needle guide 450) and (i) downstream of at least a portion of the curved septum bottom surface of the septum, or (ii) beside a portion of the curved outer surface of the septum; or (b) contacts a portion of the fluid delivery device (e.g., needle guide 450 and, more specifically, tapered portion 452) that is tapered inwardly (and, more specifically, tapered inwardly in a curved manner). The open space fitting (a)(i) and (a)(ii) immediately above may be characterized as being within the body passageway.

The version of septum 460 shown in FIG. 18B is spherical but larger in size than the FIG. 14 version of septum 460. The fluid delivery device depicted partially in this figure (in combination with FIG. 14) is an example of an embodiment of the present fluid delivery devices that includes a septum having a top that is higher than, or taller or above, the top 32 of cap 30 (and, therefore, of the body of the device).

FIGS. 19A and 19B depict different embodiments of the portion of fluid delivery device 600 (FIG. 16) that includes septum 660 and the surrounding area. The version of septum 660 shown in FIG. 19A is an example of a septum that is positioned (completely) within the body passageway, and that has a flat top surface portion that lies in plane P1 (not shown) or is flush with top 32 of cap 30. The portion of septum retaining shoulder 37 of cap 30 that contacts the FIG. 19A septum 660 is tapered outwardly at an angle of constant taper. Opening 34 may be characterized as tapering outwardly. The FIG. 19A version of septum 660 also may be characterized as having an upper portion positioned within the uppermost portion (e.g., opening 34) of the body passageway.

The FIG. 19B version of cap 30 includes an opening 34 that has an uppermost portion that is cylindrical in shape and that possesses a constant diameter. Thus, the version of opening 34 shown in FIG. 19B may be characterized as having a non-tapered upper portion (or, more specifically, uppermost portion). The version of the body passageway shown (partially) in FIG. 19B may be characterized as having a non-tapered upper portion (or, more specifically, uppermost portion).

Figure 20A:
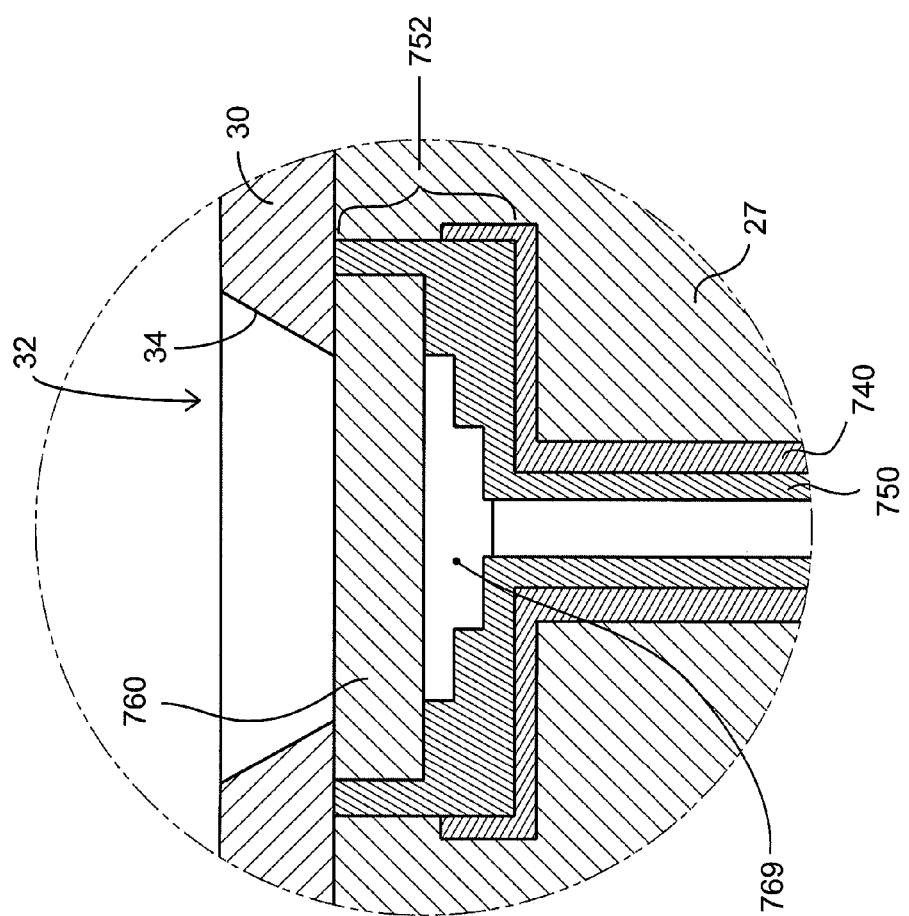
FIG. 20A is an enlarged detail view showing a different configuration of the portion of the fluid delivery device shown in FIG. 17 that includes, and is located around, the septum.

FIG. 20A shows a different version of the septum and surrounding area of fluid delivery device 700 depicted in FIG. 17. The embodiment of septum 760 shown in FIG. 20 has a width to height ratio that is less than the same ratio of the version of septum 760 shown in FIG. 17. The upper portion 752 of needle guide 750 does not have a taper of constant angle. Instead, it has an upper needle guide passageway wall portion that has a profile that decreases in size (specifically, in a stair-stepped manner) moving in a direction from upstream to downstream.

Figure 20B:
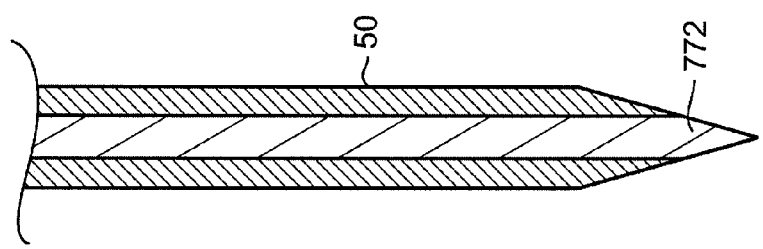
FIG. 20B is an enlarged detail view showing one embodiment of a cannula having a tapered end.

FIG. 20B shows an example of an embodiment of cannula 50 that has been tapered to match the taper of a centerpoint version of insertion needle 72. Such a taper may be used with any of the present fluid delivery devices. Some factors that tend to reduce crimping of a cannula during insertion of a given embodiment of the present fluid delivery devices include (a) the length of the taper, if any, at the end of the cannula (the longer the taper (e.g., the more gradual the angle of taper), the less likely the cannula is to crimp from the axial insertion force); (b) the diameter of the cannula (the wider the cannula, the more distributed the axial insertion force on the cannula); and (c) the thickness of the cannula wall (the thicker the wall thickness, the more distributed the axial insertion force on the cannula).

FIGS. 21A and 21B are examples of different embodiments of the upper portion, including and surrounding a septum, of the present fluid delivery devices. In both of these embodiments, no portion of septum 860 is positioned within opening 834 of cap 30, which opening has an upper portion 834a having an angle of constant taper (also characterizable as an upper tapered portion), and a downstream cylindrical portion 834b having a constant diameter. The septum retaining shoulder of cap 30 of these embodiments extends downwardly and into the base passageway of base 20; the septum retaining shoulder also may be characterized as breaking the plane of base 20. Septum 860 of both embodiments is positioned within the needle guide 850 and, more specifically, the upper tapered portion 852 of the needle guide. A portion of septum 860 is positioned within cannula 840. FIG. 21A shows an example of a septum having a top surface (more specifically, a flat top surface positioned in a plane parallel to and downstream of plane P1 depicted earlier) that is flush with the top (more specifically, the top edge) of a needle guide. FIG. 21B shows an example of a septum having a top surface (more specifically, a flat top surface positioned in a plane parallel to and downstream of plane P1 depicted earlier) that is recessed below the top (more specifically, the top edge) of a needle guide.

Figure 22:
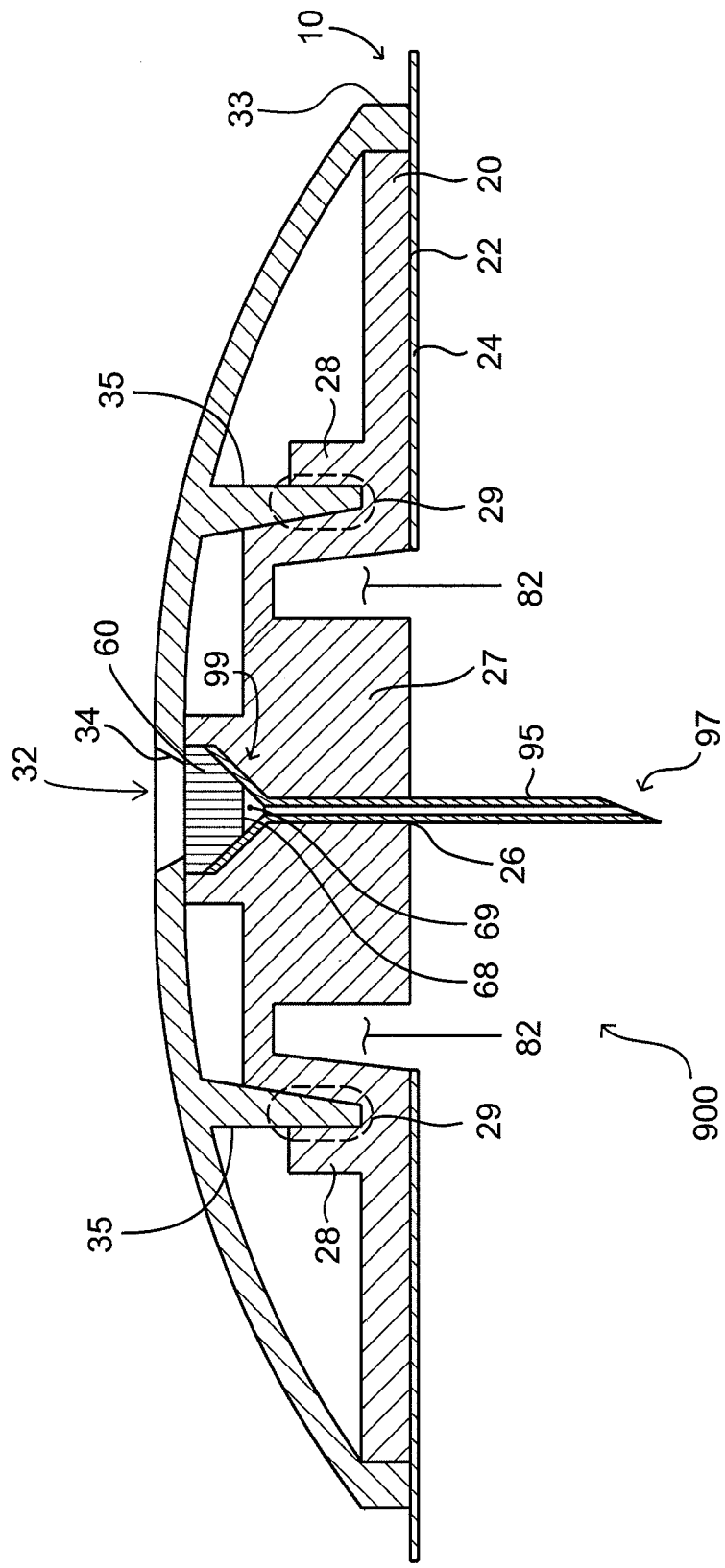
FIG. 22 is a cross-sectional view of an embodiment of the present fluid delivery devices that includes a rigid cannula.

FIG. 22 depicts an embodiment of the present fluid delivery devices—fluid delivery device 900—which includes body 10 (including cap 30 and base 20), septum 60, and cannula 95. In this embodiment, body 10 has a single inlet in communication with its body passageway. Fluid delivery device 900 does not include a needle guide because cannula 95 has a sharp end 97, which may be a centerpoint end or a beveled end (as shown) and which in some embodiments may be characterized as a "tipped" end, and is sufficiently rigid that its lower portion can be inserted into a living being without using an insertion needle, such as insertion needle 72. Taken along a plane oriented parallel to bottom surface 22, the diameter of the portion of cannula 95 that defines sharp end 97 decreases in size as one moves down the cannula and away from bottom surface 22. As the figure shows, the diameter of the shaft (taken along the same plane) is greater than the diameter at any location along the portion defining sharp end 97. Any of the cannula and needle guide combinations shown in the figures or in any of the other embodiments of the present fluid delivery devices may be replaced with cannula 95. Cannula 95 includes a cannula passageway 91 having an upper portion that is bounded by upper tapered portion 99 (which also may be characterized as having a taper of constant angle). The lower portion of cannula passageway 91 is cylindrical in shape and possesses a constant diameter that is sized to mate with the diameter of the injection needle that may be used to deliver fluid through cannula 95 and into a user. The portion of cannula 95 bounding this lower portion of cannula passageway 91 is the shaft of the cannula, and may be characterized as a straight shaft. As FIG. 22 shows, there is open space positioned between septum 60 and the shaft of cannula 95, and the open space occupies a volume that is less than the volume of the septum. Fluid delivery device 900 is an example of a fluid delivery device that is configured such that any open space that is below the septum and within the body passageway is in fluid communication with the cannula passageway.

Although not shown, the non-tipped portion of cannula 95 that extends from the bottom surface 22 of base 20 (which also may be characterized as the bottom surface of body 10) may be smaller in diameter than the portion of cannula 95 within the body passageway because the lower cannula portion need not be sized to accept an injection structure of any kind. A portion of septum 60 is positioned within cannula 95 and, more specifically, within tapered portion 99 of cannula 95.

The portion of septum 60 in contact with cannula 95 may be characterized as being supported from below (when the fluid delivery device is oriented as shown in the figure such that cannula 95 points to the ground). The portion of septum 60 in contact with cannula 95 is angled with respect to the shaft of the cannula such that the surface defining that septum portion may be characterized as a portion (more specifically, a lower outer surface portion) that is not parallel with the shaft of the cannula (or with a longitudinal axis (not shown) centered in cannula 95), septum 60 having lower support at one or more locations on that portion.

Fluid delivery device 900 is an example of a fluid delivery device that is configured such that fluid passing from beneath septum 60 to sharp end 97 of cannula 95 is uninterrupted by non-cannula structure (structure other than the cannula or some portion of the cannula, like a coating on the cannula). Fluid delivery device 900 also is an example of a fluid delivery device that lacks any non-cannula structure positioned between septum 60 and cannula 95.

As with each of the embodiments of the present fluid delivery devices, any of the features of a first embodiment of the present fluid delivery devices may be used with any other embodiment provided they are not inconsistent with the features of the other embodiment. For example, the adhesive layer 24 of fluid delivery device 900 may be configured as shown in FIGS. 8A and 8B. As another example, fluid delivery device 900 may be configured as shown in FIG. 10, such that an injection needle (such as injection needle IN1, IN2 or IN3 shown in FIG. 10) that has passed through the septum (e.g., septum 60) to deliver medication to a living being during use of the fluid delivery device either (a) exits the septum into an open space (e.g., open space 69) that is within the body passageway and downstream of at least a portion of the septum bottom surface (e.g., bottom surface 68), or (b) contacts a portion of the fluid delivery device (e.g., cannula 95 and, more specifically, upper tapered portion 99) that is tapered inwardly.

Figure 23:
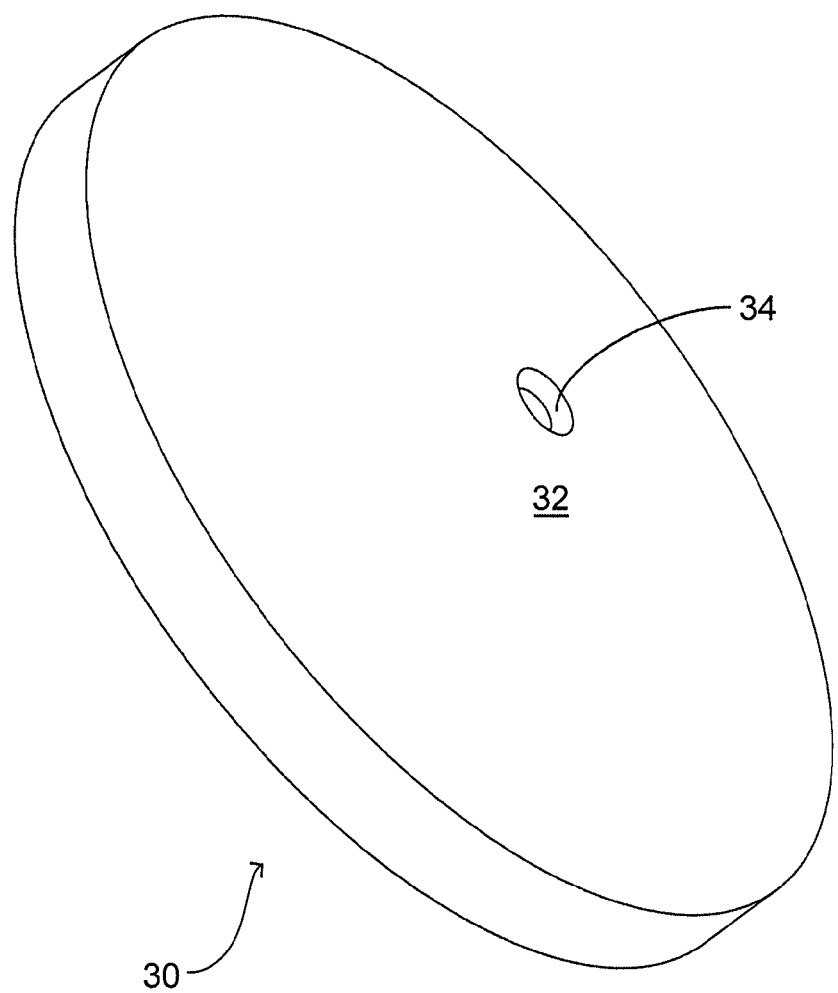
FIGS. 23 and 24 are perspective views of different caps that may be used with some embodiments of the present fluid delivery devices.
Figure 24:
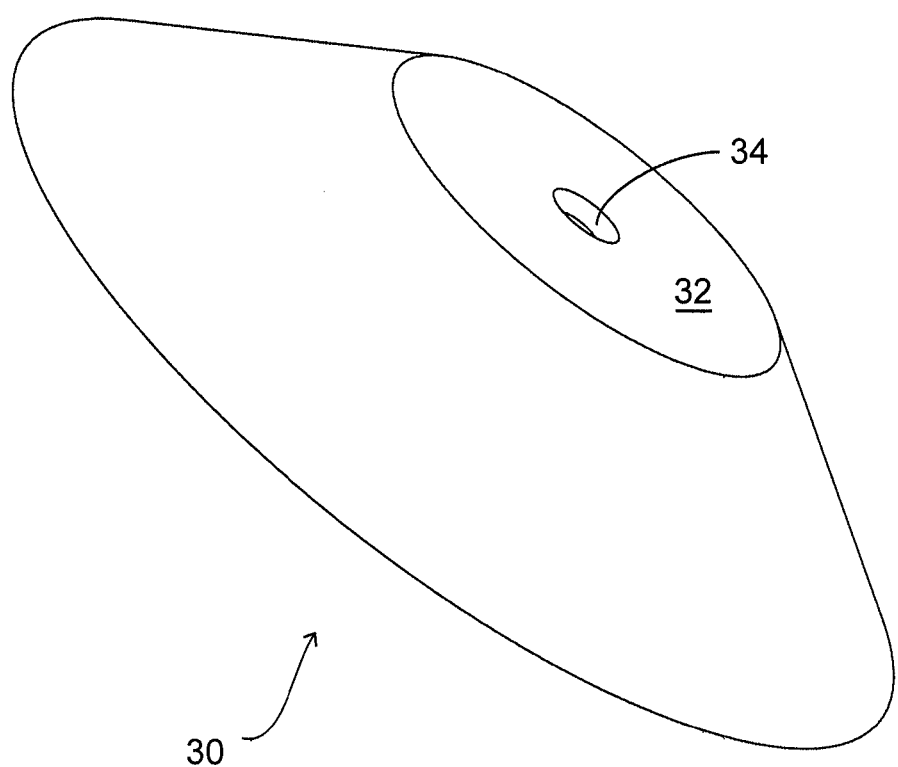

The outer configuration of the caps shown in the figures may be altered as desired to best fit the preference of user or group of users. For example, FIGS. 23 and 24 are top perspective views of different versions of cap 30 that may be used in place of the versions of cap 30 shown in the other figures.

The present fluid delivery systems may include one or more of the present fluid delivery devices that are sterilized (e.g., with ethylene oxide) and sealed in a package (such as package 250 shown in FIG. 11B), which may take the form of a pouch, tray, box, tube, or the like. The package may include instructions for use on the outside of the package or on material (e.g., a folded piece of paper) placed in the package. The systems also may include an injection device, such as a standard syringe, and/or a vial or vials of fluid to be delivered to the user (such as insulin).

The materials from which the elements of the present fluid delivery devices may be made should be biocompatible. The septa that may be used with some embodiments of the present fluid delivery devices may be characterized as self-sealing septa, or resealing septa, and may be made from a resilient material. One example of a suitable material for such septa is silicone elastomer, although other materials may be used. If the injection structure chosen to inject fluid into a given embodiment of the present fluid delivery devices is an injection needle, the injection needle used should be sized such that the septum will reseal when the needle is withdrawn. For example, the needle size should be chosen in light of the septum material and the radial pressure the needle will exert on the septum material it contacts such that the needle does not leave a septum opening when withdrawn that is large enough for contaminants to leak downstream into the fluid delivery device, or, likewise, fluid to leak upstream out of the fluid delivery device.

The bodies of the present fluid delivery devices (e.g., both the caps and bases of the two-piece bodies) may be made from many different materials, such as any suitable medical grade plastic. The insertion hubs (or handles) (e.g., insertion hub 74) of the present fluid delivery devices that include them and the insertion needle covers (e.g., insertion needle cover 76) of the present fluid delivery devices that include them also may be made, for example, from any suitable medical grade plastic. The insertion structures (e.g., insertion needle 72) of the present fluid delivery devices that include them may be made from any suitable material, such as stainless steel or a suitably rigid polymer. The needle guides (e.g., needle guide 50) of the present fluid delivery devices that include them may be made from any suitable material, such as stainless steel, although other materials may be used. The embodiments of the present needle guides that are made from metal, such as an alloy, may be characterized as metal needle guides. The soft cannulas (e.g., cannula 40) of the present fluid delivery devices that include them may be made from many different materials, such as any suitable medical grade plastic. Those that are not made from metal may be characterized as non-rigid cannulas or non-metal cannulas.

The needle guards (e.g., needle guard 80) of the present fluid delivery devices that include them may be made from many different materials, such as any suitable medical grade plastic. The adhesive layers or pads (e.g., adhesive layer 24) of the present fluid delivery devices that include them may be made from any suitable material, and any adhesive that is used may include an anti-bacterial and/or healing promotion substance (such as dexamethasone, or the like) that reduces the risk of infection and speeds the healing process once the fluid delivery device is removed from the user. The rigid cannulas (e.g., cannula 95) of the present fluid delivery devices that include them may be made from any suitable material—such as stainless steel, any suitable alloy or any suitably rigid polymer. Versions of the present rigid cannulas that are made from metal may (in such embodiments) be characterized as metal cannulas.

If a medical grade plastic is used for one of the elements discussed above, the material chosen may, be translucent, transparent, semi-transparent, or opaque in different embodiments.

Embodiments of the present fluid delivery devices that use a soft cannula may be installed using any well-known and appropriately configured insertion device, such as the insertion devices shown in FIGS. 1-4. Installing one of the present fluid delivery devices to a user using such an insertion device may be characterized as non-spring driven installation, or installation using force applied directly by hand. Other suitable insertion devices include those that are triggered by releasing the potential force built up in a compressed spring. Installation using a spring-driven device may be characterized as spring-driven installation. Still other insertion devices could be computer-controlled. Other forces that may be used to install one of the present fluid delivery device to a user include pneumatic and hydraulic forces. In general, installation of the embodiments of the present fluid delivery devices that include non-rigid cannulas without any reinforcing coating should be relatively quick and forceful to reduce the chance of the cannula crimping or bending during insertion. The installation of embodiments that include a rigid cannula or a non-rigid cannula that has been reinforced in some manner may be achieved more slowly and, in some cases, with less force.

As an alternative to the use of insertion devices with needles for installing embodiments of the present fluid delivery devices that have a non-rigid cannula, an outer surface of the exposed portion of the cannula may be coated with a fluid soluble coating that provides a sharp tip, or point, at the end of the cannula, but that dissolves in the bodily fluids of the user after insertion. Such a coating is described in paragraphs 0035 to 0045 of U.S. Patent Application Pub. No. 2002/0072720, which paragraphs are incorporated by reference.

Different injection devices may be used to facilitate the delivery of fluid to, for example, the subcutaneous tissue of a user. For example, a standard syringe and syringe needle may be used. The syringe needle may be sharp and open at its end, sharp and open somewhere along its shaft other than at its end, blunt and open at its end, or blunt and open somewhere along its shaft other than at its end. Other suitable injection devices include pen-like devices having some sort of needle that is generally concealed. Injection of fluid into a patient using one of these injection devices may be characterized as delivering fluid to a user from a non-pump source, or delivering fluid to a user from a source that is not connected to a pump. The fluid delivery may take place without the use of a fluid delivery line that is positioned completely outside of the user and at least partially outside of the body of the fluid delivery device (such as the flexible conduit that would otherwise connect a pump to the fluid delivery device). Delivering fluid in this fashion (e.g., without the use of a pump and/or a fluid delivery line connecting a pump to the fluid delivery device) helps to minimize dead space.

In other embodiments of the present devices, systems and methods, a pump may be used in the fluid delivery process. Thus, other embodiments of the present devices may be configured to facilitate the use of a pump for fluid delivery.

While the target tissue of a patient may be pinched and/or pulled outwardly from the body slightly to isolate it, insertion of the cannula of one of the present fluid delivery devices into the tissue of a user still may, in some embodiments, be characterized as being at a substantially perpendicular angle to a target skin location of a user/living being because the rigid cannula or non-rigid cannula and insertion structure will enter the user's tissue at an angle that is substantially perpendicular to the plane in which the target tissue lies.

Some embodiments of the present methods include the use of the insertion and/or injection techniques described above.

The present fluid delivery devices, systems and methods are not intended to be limited to the particular forms disclosed. Rather, they include all modifications, equivalents, and alternatives falling within the scope of the claims. For example, as discussed briefly above, although the embodiments of the present fluid delivery devices shown in the figures include bodies that are comprised of two major pieces, bodies having only one major piece and a small seal configured to retain the septum may be used instead. Furthermore, a body comprising three or more pieces also may be used.

As another example, although the soft cannulas shown in the figures are separate from, but coupled to, the bodies shown in those figures, other embodiments of the present fluid delivery devices include bodies that are integrally formed with a cannula, such that the cannula extends downwardly from the bottom surface of the body, but does not extend back up into the body.

As another example, multiple cannulas may extend from and be coupled to a body of one of the present fluid delivery devices such that the delivery of medication may be spread to different areas of a user's tissue. For example, a body may be configured with a single body opening (such as opening 34) that feeds, for example, a primary needle guide and soft cannula combination that is in fluid communication with multiple soft or rigid cannulas that deliver fluid to target tissue locations.

As another example, in some embodiments of the present infusion systems, the package containing one or more of the present fluid delivery devices also may include one or more capsules, or vials, containing a prescribed amount of fluid.

As another example, the upper portion of the body passageway (including the body opening) may be set at an angle other than 90 degrees (e.g., any suitable acute angle) to the bottom surface of the body. Similarly, the portion of the cannula that is exposed when not inserted into a user (the lower portion of the cannula) may be set at a non-perpendicular angle (e.g., any suitable acute angle) to the bottom surface of the body.

As another example, the embodiments of the present fluid delivery devices shown in the figures (thus, some embodiments of the present fluid delivery devices) have needle guides with stems (or sections having a cross-section that is substantially identical along the lower portion of the needle guide) and are configured such that at least some open space exists above the stem and below the bottommost portion of the septum. In other embodiments, the bottommost portion of the septum may extend downstream such that there is less such open space than what is shown in the figures (even FIG. 18A) down to no such open space. In some embodiments of the present fluid delivery devices, one may want to put the length (or thickness) of the septum in compression such that the resulting radial force exerted by the septum on the needle guide (and, thus, the friction force restricting upstream and downstream movement of the septum relative to the needle guide) is as high as is desired. Having at least some open space beneath the bottommost portion of the septum and the uppermost portion of the stem of the needle guide may facilitate such compression.

The claims are not to be interpreted as including means-plus- or step-plus-function limitations, unless such a limitation is explicitly recited in a given claim using the phrase(s) "means for" or "step for," respectively.

We claim:

1. A fluid delivery device comprising:
a body having a body passageway, a top, a bottom surface, a first perimeter at the top, and a second perimeter close to the bottom surface, the first perimeter being positioned in a first plane that is perpendicular to an axis that is parallel to a portion of the body passageway, the second perimeter being positioned in a second plane that is parallel to the first plane, and the second perimeter being greater than the first perimeter, the body lacking a substantially-rectangular skin-contacting wing extending at an acute angle from an adjacent upstream body portion;
a cannula having a cannula passageway and a portion extending from the bottom surface;
a needle guide having a portion positioned within the cannula passageway and a tapered portion having a length; and
a septum having a portion in contact with the tapered portion of the needle guide for at least half of the length;
the fluid delivery device being configured to adhere to a living being's skin.

2. The fluid delivery device of claim 1, where the configuration is achieved with an adhesive layer.

3. A fluid delivery device comprising:
a body having a body passageway, a top, a bottom surface, a first perimeter at the top and a second perimeter close to the bottom surface, the first perimeter being positioned in a first plane that is perpendicular to an axis that is parallel to a portion of the body passageway, the second perimeter being positioned in a second plane that is parallel to the first plane, the second perimeter being greater than the first perimeter;
a cannula having a portion extending from the body, a cannula passageway, and an upper tapered portion;
a needle guide having a tapered portion in contact with the upper tapered portion of the cannula; and
a septum having a portion positioned within the needle guide.

4. A fluid delivery device comprising:
a body having a body passageway and an outer perimeter;
a cannula having a cannula passageway and a portion extending from the body, the cannula being positioned such that any portion of the cannula that is outside a living being's skin when the fluid delivery device is used is positioned within the outer perimeter of the body;
a needle guide having a portion positioned within the cannula passageway and a tapered portion having a length; and
a septum having a septum bottom surface and a portion in contact with the tapered portion of the needle guide for at least half of the length, the septum also having a greatest width and a greatest length, the greatest width being larger than the greatest length;
the fluid delivery device being configured such that an injection needle that has passed through the septum to deliver medication to a living being during use of the fluid delivery device either (a) exits the septum into an open space that is within the body passageway and downstream of at least a portion of the septum bottom surface, or (b) contacts a portion of the fluid delivery device that is tapered inwardly.

5. A fluid delivery device comprising:
a body having a body passageway;
a cannula having a portion extending from the body, a cannula passageway, and an upper tapered portion;
a needle guide having a needle guide passageway and a tapered portion in contact with the upper tapered portion of the cannula; and
a septum having a septum bottom surface and a portion positioned within the needle guide passageway;
the fluid delivery device being configured such that an injection needle that has passed through the septum to deliver medication to a living being during use of the fluid delivery device either (a) exits the septum into an open space that is within the body passageway and downstream of at least a portion of the septum bottom surface, or (b) contacts a portion of the fluid delivery device that is tapered inwardly.

6. A fluid delivery device comprising:
a body having a body passageway and an outer perimeter;
a cannula having a cannula passageway and a portion extending from the body, the cannula being positioned such that any portion of the cannula that is outside a living being's skin when the fluid delivery device is used is positioned within the outer perimeter of the body, the cannula having a tapered portion;
a needle guide having a portion positioned within the cannula passageway and a tapered portion having length, the tapered portion of the needle guide being in contact with the tapered portion of the cannula; and
a septum having a septum bottom surface and a portion in contact with the tapered portion of the needle guide for at least half of the length;
the septum bottom surface being configured and the septum being positioned such that if an injection needle that has passed through the septum to deliver medication to a living being during use of the fluid delivery device exits the septum bottom surface into an open space, the open space is within the body passageway and downstream of at least a portion of the septum bottom surface.

* * * * *

UNITED STATES PATENT AND TRADEMARK OFFICE
CERTIFICATE OF CORRECTION

| | | |
|---|---|---|
| PATENT NO. | : 8,551,047 B2 | Page 1 of 1 |
| APPLICATION NO. | : 11/466349 | |
| DATED | : October 8, 2013 | |
| INVENTOR(S) | : Burns et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 798 days.

Signed and Sealed this
Twenty-fourth Day of February, 2015

Michelle K. Lee
*Deputy Director of the United States Patent and Trademark Office*